United States Patent
Goldstein

(10) Patent No.: US 7,171,371 B2
(45) Date of Patent: Jan. 30, 2007

(54) METHOD AND SYSTEM FOR PROVIDING PRE AND POST OPERATIVE SUPPORT AND CARE

(75) Inventor: Steven Goldstein, Boca Raton, FL (US)

(73) Assignee: SMG Trust, Delray Beach, FL (US)

( * ) Notice: Subject to any disclaimer, the term of this patent is extended or adjusted under 35 U.S.C. 154(b) by 552 days.

(21) Appl. No.: 09/725,406

(22) Filed: Nov. 29, 2000

(65) Prior Publication Data

US 2001/0021910 A1  Sep. 13, 2001

Related U.S. Application Data

(63) Continuation-in-part of application No. 09/444,124, filed on Nov. 19, 1999, which is a continuation-in-part of application No. 09/390,530, filed on Sep. 3, 1999.

(51) Int. Cl.
*G06Q 10/00* (2006.01)

(52) U.S. Cl. .............................. 705/2; 705/3
(58) Field of Classification Search ............... 705/2–4, 705/10, 26; 600/300
See application file for complete search history.

(56) References Cited

U.S. PATENT DOCUMENTS

| | | |
|---|---|---|
| 4,858,121 A | 8/1989 | Barber et al. |
| 4,916,611 A | 4/1990 | Doyle, Jr. et al. |
| 5,065,315 A | 11/1991 | Garcia |
| 5,072,383 A | 12/1991 | Brimm et al. |
| 5,099,424 A | 3/1992 | Schneiderman |
| 5,301,105 A | 4/1994 | Cummings, Jr. |
| 5,361,202 A | 11/1994 | Doue |
| 5,583,758 A | 12/1996 | McIlroy |
| 5,644,778 A | 7/1997 | Burks et al. |
| 5,664,207 A | 9/1997 | Crumpler et al. |
| 5,748,907 A | 5/1998 | Crane ............................ 705/2 |
| 5,764,923 A | 6/1998 | Tallman et al. ................ 705/3 |
| 5,823,948 A | 10/1998 | Ross, Jr. et al. ............ 600/300 |
| 5,826,237 A | 10/1998 | Macrae et al. ................. 705/2 |
| 5,832,447 A | 11/1998 | Rieker et al. ................... 705/2 |

(Continued)

OTHER PUBLICATIONS

Roan, Shari, "Changing Their role; By mixing celebrity and cyberspace, some high-profile doctors are redefining the way medicine is practiced and promoted", The Los Angeles Times, Jan. 24, 2000, Part S, p. 1.*

(Continued)

*Primary Examiner*—Joseph Thomas
*Assistant Examiner*—Vivek Koppikar
(74) *Attorney, Agent, or Firm*—Jon A. Gibbons; Fleit, Kain, Gibbons, Gutman, Bongini & Bianco P.L.

(57) ABSTRACT

The present invention provides a system for providing support and care to persons considering or undergoing a medical procedure. The system includes a means for a provider to receive, process, and provide information regarding the persons to and from the persons and medical practitioners. Similarly, means for the provider to; provide information and positive reinforcement to the persons regarding said medical procedure being considered or undergone; to schedule and coordinate medical consultations and said medical procedure between said persons and said medical practitioners, and to receive, process, and deliver care orders and medicaments from said medical practitioners to said persons are also includes.

32 Claims, 21 Drawing Sheets

U.S. PATENT DOCUMENTS 5,935,060 A * 8/1999 Iliff .......................... 600/300
6,208,973 B1 * 3/2001 Boyer et al. ................ 705/2
6,249,809 B1 * 6/2001 Bro .......................... 709/217
6,283,761 B1 * 9/2001 Joao ......................... 434/236

OTHER PUBLICATIONS

Lade, Diane C., "Cyber Docs People with a Wide Range of Medical Problems are Finding Support Online from Doctors and Other patients like Themselves", Sun Sentinel, Mar. 22, 1998, p. 1E.*

* cited by examiner

Initial Information Delivery and Permission Marketing Process Flow

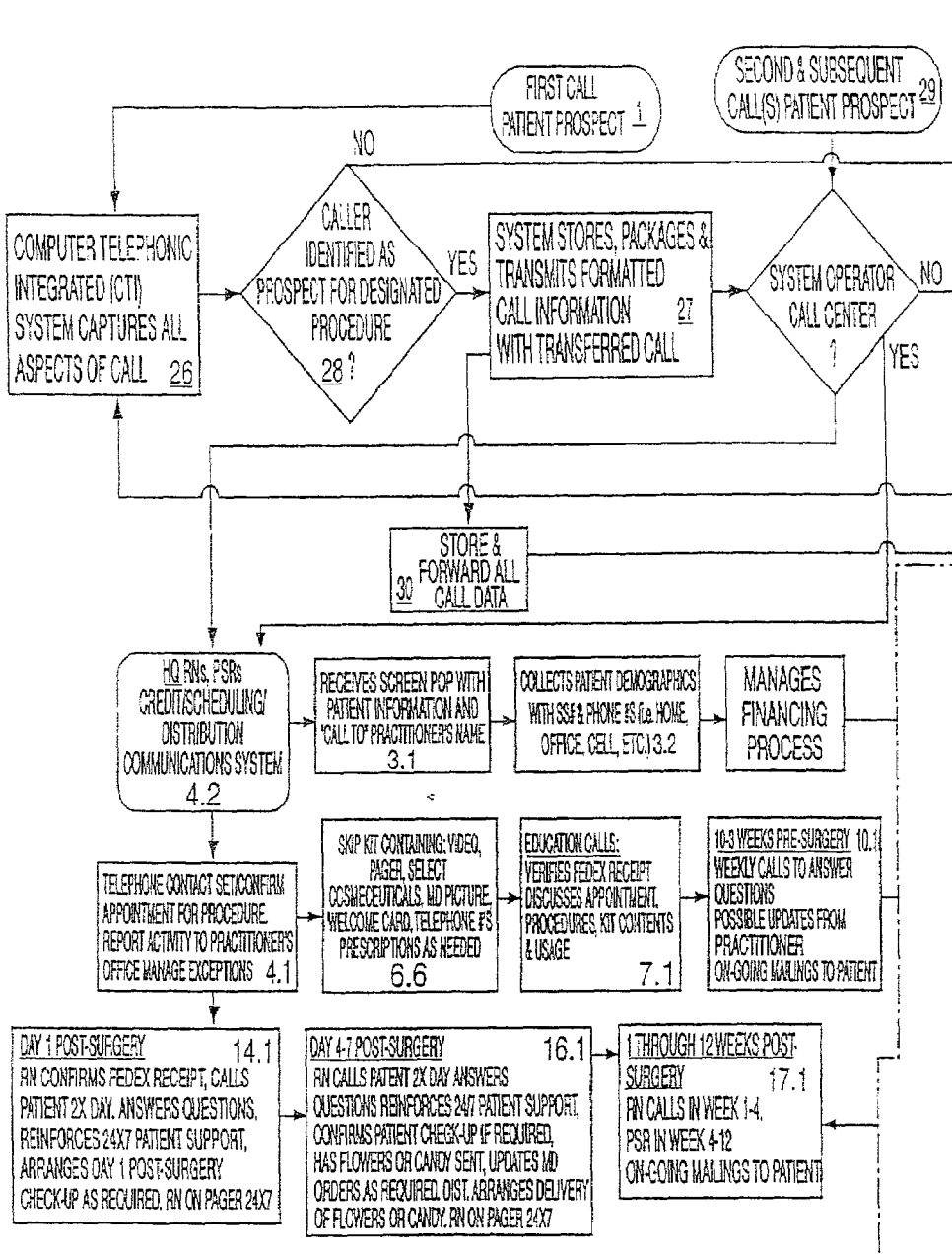
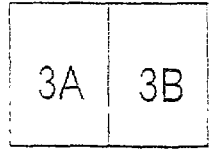
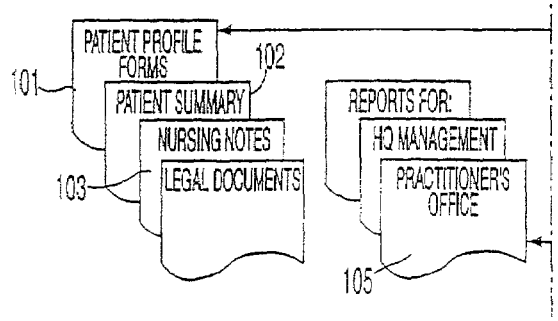
FIG. 3A
FIG. 3

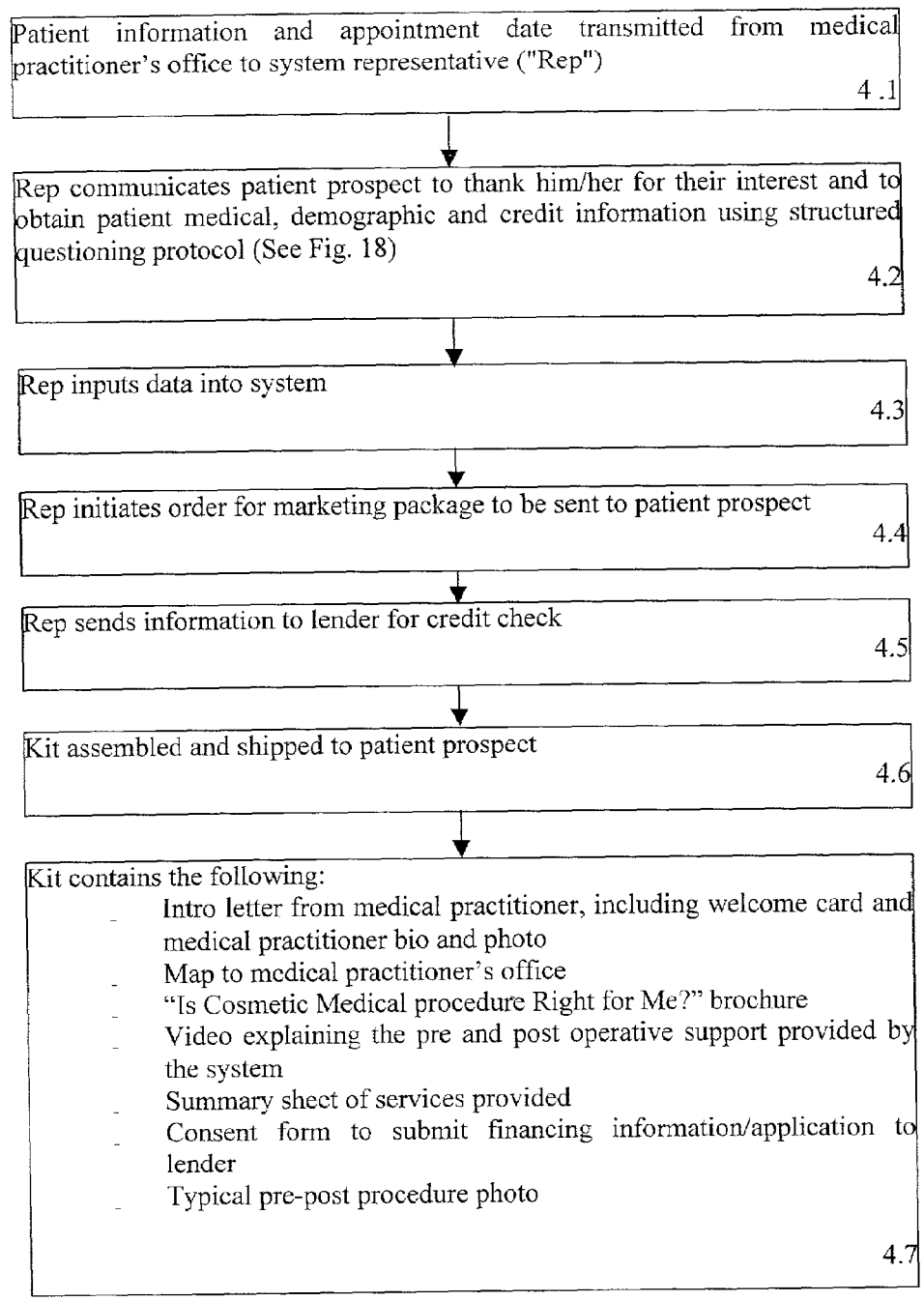

Fig. 4

INITIAL CALL BY PATIENT PROSPECT TO MEDICAL PRACTITIONER

Patient information and appointment date transmitted from medical practitioner's office to system representative ("Rep")
4.1

Rep communicates patient prospect to thank him/her for their interest and to obtain patient medical, demographic and credit information using structured questioning protocol (See Fig. 18)
4.2

Rep inputs data into system
4.3

Rep initiates order for marketing package to be sent to patient prospect
4.4

Rep sends information to lender for credit check
4.5

Kit assembled and shipped to patient prospect
4.6

Kit contains the following:
- Intro letter from medical practitioner, including welcome card and medical practitioner bio and photo
- Map to medical practitioner's office
- "Is Cosmetic Medical procedure Right for Me?" brochure
- Video explaining the pre and post operative support provided by the system
- Summary sheet of services provided
- Consent form to submit financing information/application to lender
- Typical pre-post procedure photo 4.7

PRE-APPOINTMENT STAGE

Fig. 6

DAY OF APPOINTMENT

| Rep generates patient profile form 101 and transmits to medical practitioner's office for medical practitioner/nurse use | 6.1 |

↓

| Medical practitioner or nurse transmits patient update to patient profile form 101, categorizing the patient as "Medical procedure Scheduled," "Undecided," "No," "Did not Show" | 6.2 |

↓

| For patients that scheduled medical procedure, medical practitioner/nurse transmits medical practitioner's orders and medical practitioner's authorization for payment through lender | 6.3 |

↓

| Rep inputs appointment information into system | 6.4 |

↓

| For undecided, no, no shows, 1 of 4 kits is delivered to patient, including additional information | 6.5 |

POST-APPOINTMENT STAGE FOR PATIENTS WHO SCHEDULE PROCEDURE

Fig. 8

EDUCATION FOR PATIENTS WHO SCHEDULE PROCEDURE

| Rep verifies delivery of pre-operative kit by contacting patient and initiates previous scheduled call to patient to discuss appointment, procedure, and package (pager, video and kit) 8.1 |
|---|

▼

| Rep transmits patient profile form 101 which includes confirmation of shipment and notes from conversation to medical practitioner 8.2 |
|---|

Fig. 10

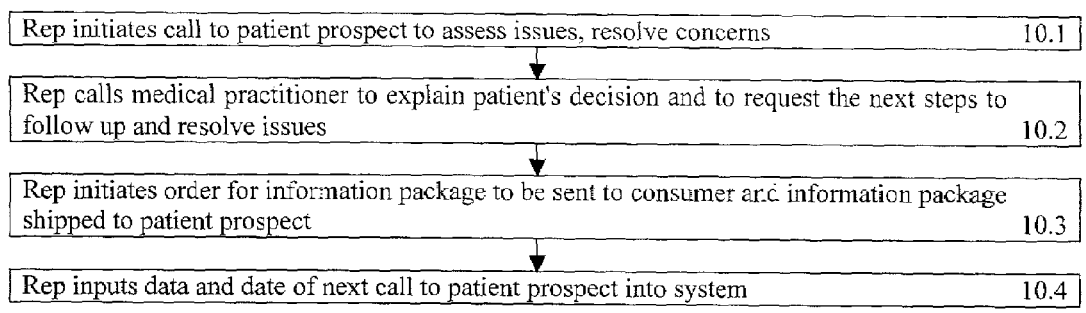

POST-APPOINTMENT STAGE FOR PATIENTS
THAT CANCEL SCHEDULED PROCEDURE

| Rep initiates call to patient prospect to assess issues, resolve concerns | 10.1 |
| Rep calls medical practitioner to explain patient's decision and to request the next steps to follow up and resolve issues | 10.2 |
| Rep initiates order for information package to be sent to consumer and information package shipped to patient prospect | 10.3 |
| Rep inputs data and date of next call to patient prospect into system | 10.4 |

Fig. 11

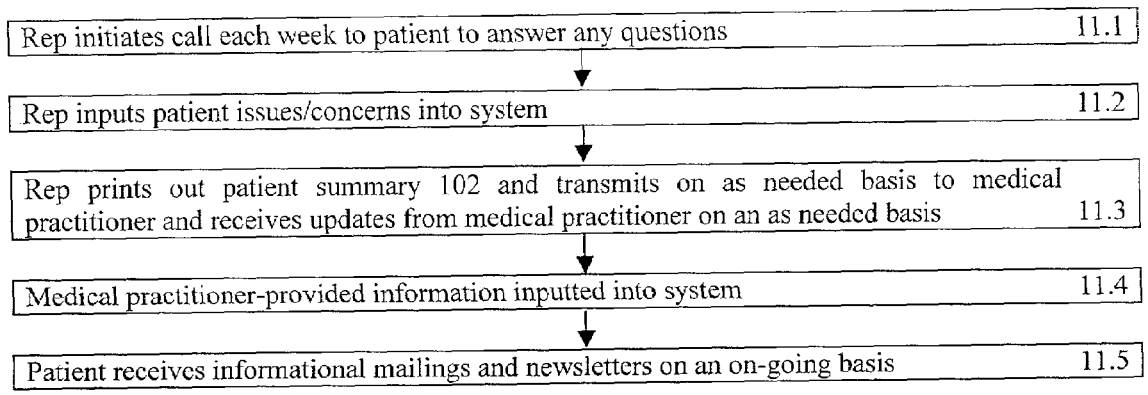

10 WEEKS THROUGH 3 WEEKS PRIOR TO PROCEDURE

| Rep initiates call each week to patient to answer any questions | 11.1 |

↓

| Rep inputs patient issues/concerns into system | 11.2 |

↓

| Rep prints out patient summary 102 and transmits on as needed basis to medical practitioner and receives updates from medical practitioner on an as needed basis | 11.3 |

↓

| Medical practitioner-provided information inputted into system | 11.4 |

↓

| Patient receives informational mailings and newsletters on an on-going basis | 11.5 |

DAY BEFORE PROCEDURE

DAY OF PROCEDURE

PRIOR TO, AND DAY OF FIRST POST-PROCEDURE VISIT

Fig. 17

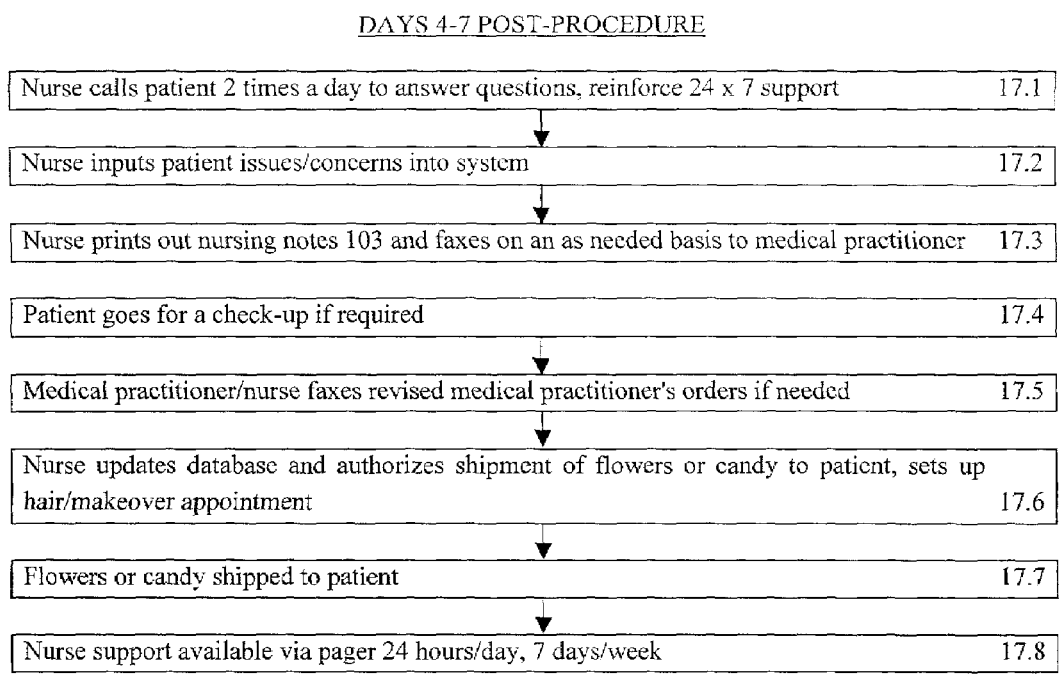

DAYS 4-7 POST-PROCEDURE

| | |
|---|---|
| Nurse calls patient 2 times a day to answer questions, reinforce 24 x 7 support | 17.1 |
| Nurse inputs patient issues/concerns into system | 17.2 |
| Nurse prints out nursing notes 103 and faxes on an as needed basis to medical practitioner | 17.3 |
| Patient goes for a check-up if required | 17.4 |
| Medical practitioner/nurse faxes revised medical practitioner's orders if needed | 17.5 |
| Nurse updates database and authorizes shipment of flowers or candy to patient, sets up hair/makeover appointment | 17.6 |
| Flowers or candy shipped to patient | 17.7 |
| Nurse support available via pager 24 hours/day, 7 days/week | 17.8 |

# METHOD AND SYSTEM FOR PROVIDING PRE AND POST OPERATIVE SUPPORT AND CARE

This application is a continuation-in part of prior application Ser. No. 09/444,124, filed on Nov. 19, 1999, which in turn, is a continuation-in-part of prior application Ser. No. 09/390,530, filed on Sep. 3, 1999.

BACKGROUND OF THE INVENTION

1. Field of the Invention

The present invention relates to a method and system for providing pre and post operative information and support to patients undergoing medical procedures to enhance overall procedure outcomes and patient convenience and satisfaction, to reduce medical practitioner and staff time spent on routine but often unperformed communicative aspects of medical procedures, and for increasing revenues for medical practitioners by developing useful patient profiles, by facilitating procedure financing and payment, scheduling, and by providing an integrated system for sales of pre and post operative products and services.

2. Description of Related Art

According to statistics from the American Association of Cosmetic Surgery, approximately 3.3 million cosmetic or aesthetic procedures were performed in 1996, a 22% increase from 2.7 million procedures in 1994. Since 1992, cosmetic procedures have increased by 153%. It is also estimated that over $4 billion in physician fees were generated from such procedures in 1996. The number of cosmetic procedures increased approximately 50% between 1996 and 1998 alone. Certified plastic surgeons performed over 2.2 million plastic surgery procedures in 1998, a 44% increase in total number of procedures since 1992. This does not include procedures performed by medical practitioners in other specialties, such as dermatologists, ear-nose-throat specialists, oculoplastic specialists and others. Reconstructive procedures by plastic surgeons totaled an additional 1,169,400 procedures in 1998. The number of products that claim to slow down the aging process or function as anti-aging treatments has tripled in the past five years. In 1998, at least 69 anti-aging products were introduced into the market, compared to 18 in 1993.

The number of such medical procedures is expected to continue to increase as the U.S. population as a whole continues to age, social attitudes continue to indicate wider acceptance of medical procedures for self-improvement rather than merely for critical care, and as such procedures are improved and further developed with improved medical technology.

Presently, patients considering undergoing medical procedures often react with confusion and discouragement when they contact a medical practitioner that specializes in the type of procedure under consideration. Patients considering undergoing such procedures commonly suffer from low self-esteem and self-confidence, which drives their desire to improve themselves through the procedure under consideration. Such patients have a heightened need for information about what the procedure under consideration will and will not do for them, about what can be expected through the process, and about what is and is not "normal." More important, medical practitioners need to assess their patient prospects' past clinical history, their personal habits affecting their health such as substance abuse problems and psychological/psychiatric status, and their attitudes regarding healthcare providers and undergoing medical procedures. Without a thorough assessment of these various items of patient information, a medical practitioner cannot competently assess whether the contemplated medical procedure is necessary or appropriate, or whether undergoing the contemplated procedure will achieve the results desired by the patient. Identification of possible psychiatric disorders is particularly critical in the pre-operative assessment of patients contemplating elective medical procedures. Furthermore, pre-operative stress and anxiety is to be expected, post-operative depression is not unusual, and these patient mental factors can lead to actions by patients that affect the outcome of the medical procedure undergone as well as the patient's own opinion about their overall experience, which opinion can be expressed as negative recommendations to other patients and as a decision not to consider undergoing additional procedures in the future. At the same time this needed information must be obtained tactfully so as to avoid offending patient prospects who may believe that they are being treated as though they are mentally ill.

Patient prospects also frequently find that the procedure they are considering costs significantly more than what was anticipated. Often, they forego the procedure because they do not have the money to pay for it or have second thoughts after contacting a medical practitioner who does not seem to be receptive or attuned to their needs.

Medical practitioners often have very busy and lucrative practices that reduce their sensitivity to individual patient needs, particularly with regard to patients who cannot afford the contemplated procedure. Medical practitioners are typically clinicians and allied healthcare professionals with their strengths lying to a greater extent in their particular medical expertise (which typically does not include formal training in psychiatry) rather than their communicative skills. Their ability to charge substantial fees for the procedures they perform and maintain lucrative practices leads them to believe that they have no flaws. They are also not lenders and do not typically provide financing for the procedures they perform. Furthermore, they often have poor patient profiling and tracking systems to identify the needs of patients and market future procedures, products and ancillary services designed to meet such needs.

This combination of patient and medical practitioner characteristics results in a communication and support gap that appears to affect procedure closure rates for medical practitioners as well as overall procedure outcomes and patient satisfaction. It is estimated that the "closure" rate with regard to new patient prospects is approximately 10–20%, and only about 28% of patients become repeat patients. A recent study indicates that patient satisfaction is derived primarily from the perception that the medical practitioner engages the patient in a personal and attentive manner. When a patient is well informed of what to expect in the medical procedure being undergone and is positively reinforced about his or her decision to undertake the medical procedure, the patient is more likely to comply with pre and post operative treatment regimens. This greater compliance and positive attitude contributes to a better overall result. These needs have to date been unmet by prior art systems and methods.

Prior art methods and systems have focused on computerizing healthcare communications between medical practitioners, payors, hospitals and managed care organizations, and providing patient diagnostic templates and algorithms so that diagnoses and suggested treatments can be automated based on patient symptoms. For example, U.S. Pat. No. 5,301,105 teaches an integrated and comprehensive healthcare system that interconnects the patient, healthcare provider, bank or other financial institution, insurance company, utilization reviewer and the patient's employer. Such system merely streamlines and automates the processing of provider reimbursement and procedure authorizations from insurers, employers and other payors and the patient's lender when the patient finances a medical procedure, and assists with medical claims processing, combined with template diagnostic and treatment protocols. Similarly, U.S. Pat. No. 5,644,778 teaches a computerized medical transaction system that automates healthcare provider reimbursement from payors and improves the healthcare provider's compliance with reimbursement requirements.

Other prior art systems focusing on the computerization of healthcare information interchange between healthcare providers and payors, and systems providing diagnostic templates for frequently encountered conditions include U.S. Pat. No. 5,072,383 which teaches a medical information system with automatic updating of task lists in response to entering orders and charting interventions on associated forms. This system basically computerizes and automates the typical hospital operational and patient record-keeping functions that are otherwise accomplished through the use of handwritten forms. The objects of these inventions are increasing productivity and workflow primarily in non-elective procedures.

These systems do not address the need to educate and inform prospective patients, particularly those considering elective and aesthetic procedures, of what the procedure under consideration entails from start to finish and to provide continuing positive reinforcement and support to patients throughout the process and into the future. While an automated processing system may be helpful in healthcare administrative tasks, patients still need a human response to their questions and concerns. These needs, if they are to be met at all, still require medical practitioner and staff time that is better spent on direct patient care. There is a long-felt and unmet need for patients to receive information regarding the contemplated procedure to enable the patient to make an informed decision on whether or not to undergo such procedure, preferably in a manner that builds the patient's or patient prospects' confidence and trust in the medical practitioner.

Patient prospects considering undergoing elective and/or aesthetic medical procedures do not presently have easy and convenient access to such information and would likely find such information useful in deciding whether or not to undergo a particular procedure, and in choosing a particular medical practitioner. At the same time, such patient prospects often do not want to disclose to others that they are considering undergoing an elective or aesthetic medical procedure, and do not want to be solicited by providers of such products and services. There is therefore a need to provide a centralized and searchable source of information about elective and/or aesthetic medical procedures, those who have undergone them, and the medical practitioners who perform them, while preserving the anonymity of persons seeking such information until such time as such persons decide to disclose their identities and make contact with medical practitioners. At the same time, medical practitioners need to attract patients in a manner that patients feel well informed and in control of their decisions.

The present method serves these needs initially by utilizing a permission-marketing approach. Patient prospects are not requested to provide information about themselves and information is provided with no obligation. The patient prospect dictates what information he or she will initially receive and when and to what extent additional information is needed. When the patient prospect feels comfortable with providing identifying information and establishing contact with a live person, he or she can do so voluntarily—the patient prospect is not pressured. Once contact with a live person is established, the system provides information, support and reinforcement to the patient prospect before, during and after the medical procedure under consideration.

Additionally, medical practitioners who perform elective and/or aesthetic procedures need to better assess patient physical, psychological/psychiatric and financial characteristics at the outset to properly identify patient needs and the appropriateness of procedures under consideration. They also need means for improving patient prospect closure rates and maximizing cross-selling of additional procedures, a need that is typically not present with regard to non-elective procedures, and desire to increase their revenues through sales of pre and post operative products and services, referrals and additional procedures for existing patients. The system of the present invention also addresses these needs.

SUMMARY OF INVENTION

The present invention is a system for proactively supporting patients and patient prospects (hereinafter referred to in either case as the "patient") considering undergoing medical procedures from before their initial contact with the medical practitioner through the post-operative recovery stage and thereafter in planning future procedures. The present system educates the patient, manages the patient's expectations, assists the patient with obtaining financing for the procedure, answers all of the patient's questions, facilitates the provision of all medications and products and provides remote supervision of pre and post operative self-care. The present system also accomplishes medical practitioner/patient communicative tasks that medical practitioners often neglect to perform or do not perform completely, and improves the ratio of patient prospects to actual patients; it also provides a method for developing useful and valuable patient profiles that not only assist medical practitioners in identifying and addressing potential and current patients' needs, but also increase the potential revenues that the medical practitioner can generate through sales of pre and post operative patient care products and services.

All of these tasks are accomplished through the integrated communications system and pre and post operative information and support delivery method of the present invention.

The system in one embodiment uses the existing customer bases and built in daily traffic of operational health care organizations to offer their customer bases elective procedures. This system of marketing elective procedures has many advantages, most significantly minimizing the cost to market these procedures to the desired population versus the high cost and poor response rate of newspapers, radio, television and other traditional forms of marketing.

Major health care insurance companies typically receive tens of thousands of incoming calls per day. These calls are of a nature in which their customer base wishes to obtain more information on the personal insurance benefits, or the name of a referral doctor or other information that the customer may seek as part of their membership with the insurance company, as they are paying the insurance company for their personal health care coverage. Even though the insurance company may not pay for elective procedure, they may offer these informational services through the system of the present invention to their customers as value added services.

The health care insurance company would market elective procedures in one of two ways, first by providing callers with information while on hold. A general message on elective procedures is offered to all that call the insurance company. The customers of the insurance company could then make their own determination if they wished to find out more about these procedures and choose from a menu option which would take the interested party directly to a patient care specialist at the system end who would qualify the customer and determine if they were a likely candidate for elective procedure. The candidates who are filtered through the system would be sent to participating doctors who have joined the system as panel members. The call center maintains access to the doctors' schedule and provides scheduling at the time of the call. The doctor would see the prospective patient and determine if they were a clinical candidate for the procedure. The doctor, as a provider of the system, benefits from increased patient traffic and renders a portion of his/her fee to the system operator in exchange for marketing, qualifying and financing a new patient and forwarding the patient to them.

In the second portion of the marketing program that is employed in one embodiment of the method of the present invention, the insurance company sends out millions of pieces of mail per year. This mail is sent directly to their customers and contains information on membership, payments, and explanation of benefits for a particular physician visit. The insurance company would market elective procedures directly to their existing customers as well as new customers which they wish to procure to provide general insurance. Brochures and promotional information would be packaged to the existing customer along with their monthly existing communications from the insurance company. A special phone number would reach the system call center. The usual process of filtering, scheduling and sending patients to various doctors would take place in accordance with a preferred embodiment of the method of the present invention.

One embodiment of the present invention initially utilizes a virtual front end, physical back end permission marketing method integrating computer and voice telephony communications to provide information regarding elective and/or aesthetic medical products and services based on patient requests without obligation, to establish and cultivate a feeling of comfort and trust in the patient. Information is first provided via computer through a searchable Internet website providing information about people who have undergone various elective and/or aesthetic medical procedures. Patients can enter queries to obtain information about people who have similar demographic traits and have undergone particular medical procedures in particular geographic areas with particular medical practitioners. The information obtained includes anonymous accounts of other people's experiences in having undergone various medical procedures. The personal but anonymous accounts can also include evaluations of medical practitioners. Information is also provided by a live attendant if and when the patient decides to seek additional information and make contact with a live person.

If a patient decides to establish contact with a live person to discuss the possibility of undergoing an elective and/or aesthetic medical procedure, the person can indicate this by leaving an e-mail message, clicking on an icon on their computer screen, or otherwise providing a signal via their computer system. The patient will then be contacted promptly by a live attendant that will have any previously provided identifying information regarding the patient. The live attendant provides additional information as requested by the patient without obligation or pressure. The attendant can also, upon patient request, assist with the selection of a medical practitioner and coordinate scheduling with the selected medical practitioner, and thereafter transition the patient to a pre and post operative care system and method specifically designed to optimize the success and positive experience regarding the elective and/or aesthetic medical procedure undergone. The overall outcome and positive experience will be enhanced by the patient's perception that he or she has been treated professionally without aggressive marketing tactics—the focus being always on optimizing the patient's positive overall outcome and building a relationship of trust and confidence with the patient.

Once live person to person contact is made with a patient prospect who wants to contact a medical practitioner, the system receives and transmits relevant patient information to and from the patient and the medical practitioner, to and from the healthcare facility where the medical procedure is to be performed, and to and from a third party lenders and payors for financing and payment of the medical procedure as well as to and from other participants in the healthcare delivery network. The system compiles patient personal, psychological/psychiatric and financial/credit information and procedure scheduling data to create a useful patient management database and generates a patient profile that is used by the medical practitioner as a continually updated patient record to identify patient psychological and other medical needs as well as their need for procedure financing, which information can be utilized in the future to offer additional products and services to the patient. The database is accessible by the various participants in the delivery and payment of the particular healthcare procedure and pre and post operative products and services, with secure, tiered access available based on each such participant's need to know items of patient information. The system also generates patient specific pre and post operative care information and product kits and provides means for tracking patient receipt and usage of such information and products. It provides an organized, structured yet customizable protocol to manage patient expectations and information delivery through all stages of the contemplated medical procedure.

BRIEF DESCRIPTION OF THE DRAWINGS

FIG. 3 is a flow chart diagram describing the overall basic operation of the system in one embodiment from the initial patient prospect call stage to the post-procedure stages.

FIG. 6 describes the steps of a preferred embodiment of the present system at the first appointment stage.

FIG. 8 describes the steps of a preferred embodiment of the present system providing information and education to patients that have scheduled a medical procedure date.

FIG. 10 describes the steps of a preferred embodiment of the present system at the post- first appointment stage for patients that cancel their scheduled medical procedure date.

FIG. 11 describes the steps of a preferred embodiment of the present system during the period 10 weeks through 3 weeks prior to the scheduled medical procedure date.

FIG. 17 describes the steps of a preferred embodiment of the present system during the period from day 4 through day 7 post medical procedure.

DESCRIPTION OF A PREFERRED EMBODIMENT

Figure 1:
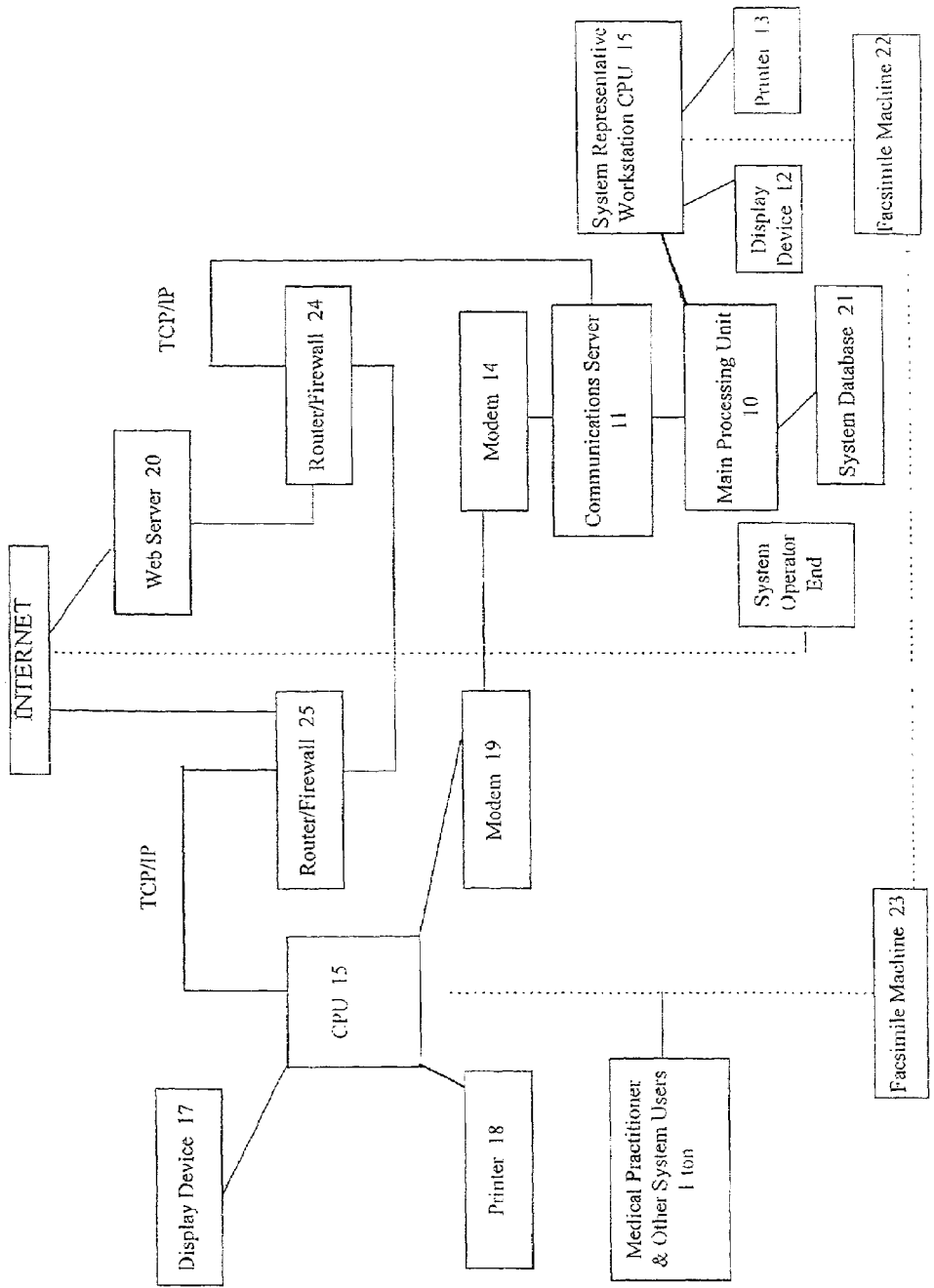
FIG. 1 is a diagram describing a preferred embodiment of the basic system architecture of the present invention.

The present system, in a preferred embodiment, comprises means for receiving, processing and providing personal, medical and financial/credit information pertaining to patients to and from patients and medical practitioners and development of a comprehensive patient profile based on such information identifying the patient's present and future needs for elective or aesthetic medical products and services and the patient's ability to pay for same; means for providing information regarding what can be expected through the process of undergoing a medical procedure and for providing positive reinforcement to patients regarding their decision to undergo a medical procedure; means for scheduling and coordinating pre and post-operative medical appointments and procedures between patients and medical practitioners; means for receiving, processing and delivering pre and post procedure care orders and medicament prescriptions from medical practitioners to patients; and means for monitoring patient adherence to medical practitioners' care orders, medical consultation and procedure schedules and medicament prescriptions.

The system, in a preferred embodiment, optionally further comprises means for receiving, transmitting and processing said patient financial/credit data to a third party lender for medical procedure financing application processing, or alternatively, means for transmitting and receiving insurer or other third party payor authorization for payment of medical consultations and procedures; means for processing medical practitioners' receipt of payment for said medical consultations and procedures through said third party lender upon patient credit and financing approval or from said insurers or other third party payors; and means for processing data regarding sales of medicaments and completion of medical procedure financing transactions attributable to each medical practitioner, and calculation of payments due to each medical practitioner based on said sales and financing.

The present system establishes real-time telecommunications links on an as needed basis between the patient, the system representative, the medical practitioner's office, third party lenders and payors such as insurers and the patient's employer, the facility where the medical procedure will be undergone, and with ancillary service providers. These communications links may be via computers utilizing modems, via voice telephony, facsimile transmission or other real-time telecommunications networks, or any combination thereof.

The present invention is also a method for delivering pre and post operative support and care to patients considering or undergoing medical procedures, comprising the steps of receiving, processing and providing information regarding said persons to and from said persons and medical practitioners, providing information and positive reinforcement to said persons regarding the procedure being considered or undergone, scheduling and coordinating medical appointments and procedures between said persons prospects and medical practitioners, receiving, processing and delivering care orders and medicaments from medical practitioners to said persons and monitoring said persons' adherence to medical practitioners' care orders, appointment and procedure schedules and medicament prescriptions. It provides a method of improving patient outcomes and patient satisfaction with regard to medical procedures undergone, by educating said patient regarding said medical procedure before it is undergone, managing said patient's expectations regarding realistic results and outcomes of said medical procedure, providing pre and post procedure medicaments, and monitoring said patients' adherence to medical practitioners' orders and self-care regimens.

The system in one embodiment uses the existing customer bases and built in daily traffic of operational health care organizations to offer their customer bases elective procedures. Major health care insurance companies typically receive tens of thousands of incoming calls per day. These calls are of a nature in which their customer base wishes to obtain more information on the personal insurance benefits, or the name of a referral doctor or other information that the customer may seek as part of their membership with the insurance company, as they are paying the insurance company for their personal health care coverage. Even though the insurance company may not pay for elective procedure, they may offer these informational services to their customers as value added services. The health care insurance company would market these elective procedures in one of two ways, first by providing callers with information while on hold. A general message on elective procedures is offered to all that call the insurance company. The customers of the insurance company could then make their own determination if they wished to find our more about these procedures and choose from a menu option which would take the interested party directly to a patient care specialists at the system end who would qualify the customer and determine if they were a likely candidate for elective procedure. The candidates who are filtered through the system would be sent to participating doctors. The doctor would see the patient and determine if they were a clinical candidate for the procedure, as a provider of the system, benefits from increased patient traffic and renders a portion of his/her fee to the system operator in exchange for marketing, qualifying and financing a new patient and forward the patient to them.

In the second portion of the marketing program that is employed in one embodiment of the method of the present invention involves providing information regarding medical procedures in mailings. Insurance companies send out numerous pieces of mail per year. The insurance company would market elective procedures directly to their existing customers as well as new customers which they wish to procure to provide general insurance. Brochures and promotional information would be packaged to the existing customer along with their monthly existing communications from the insurance company. A special phone number would reach the system call center. The usual process of filtering and sending patients to various doctors would take place in accordance with a preferred embodiment of the method of the present invention.

One embodiment of the present invention utilizes a virtual front end, physical back end permission marketing method integrating computer and voice telephony communications to provide information regarding elective and/or aesthetic medical products and services based on patient requests without obligation, to establish and cultivate a feeling of comfort and trust in the patient. Information is first provided via computer through a searchable Internet website providing information about people who have undergone various elective and/or aesthetic medical procedures. Patients can enter queries to obtain information about people who have similar demographic traits and have undergone particular medical procedures in particular geographic areas with particular medical practitioners.

If a patient decides to establish contact with a live person to discuss the possibility of undergoing an elective and/or aesthetic medical procedure, the person can indicate this by leaving an e-mail message, clicking on an icon on their computer screen, or otherwise providing a signal via their computer system. The live attendant provides additional information as requested by the patient without obligation or pressure. The attendant can also, upon patient request, assist with the selection of a medical practitioner and coordinate scheduling of an initial consultation with the selected medical practitioner, and thereafter transition the patient to a pre and post operative care system and method specifically designed to optimize the success and positive experience regarding the elective and/or aesthetic medical procedure undergone. The overall outcome and positive experience will be enhanced by the patient's perception that he or she has been treated professionally without aggressive marketing tactics—the focus being always on optimizing the patient's positive overall outcome and building a relationship of trust and confidence with the patient.

Referring now to FIG. 1, the system architecture in a preferred embodiment includes, at the system representative end, a main processing unit 10 with data storage capability, a communications server 11, a display device 12, a printer 13 and a modem 14 configured and interconnected in a conventional fashion using existing or dedicated telecommunications infrastructures to central processing unit ("CPU") systems 15 located at the system representative stations of the system headquarters as well as each of the system's other participant's facilities, which may include the medical practitioner's office, the medical facility where the contemplated medical procedure will be performed (if different), third party lenders' or other payors' facilities, pharmacies, laboratories and other ancillary service facilities, and even at the patient's location. The remote CPUs 16 have similar display devices 17, printers 18 and modems 19. The main processing unit 10 and the various remotely located CPUs 16 may also communicate via known methods utilized for Internet communications, namely, data transmission across telephone or data transmission lines through gateways interfacing with the main processing unit 10 using a protocol understood by said remote CPUs 16 (or intermediary equipment connected thereto). For example, in a preferred embodiment of the present system, data is transmitted to and from the main processing unit 10 to remote CPUs 16 via a web server 20 interconnected to said communications server 11 through the Internet using transmission control protocol/Internet protocol ("TCP/IP") with conventional router/firewall components 24 and 25.

Telephony may also be employed in the present system through the use of facsimile machines 22 and 23 to send and receive hard copy data and through the use of conventional telephones to provide voice data communication between and among the system representative and other system participants. The remote CPUs 16 in a preferred embodiment also have data storage devices commonly used in computer systems such as hard disks. The applications and operating software of the present system resides in the communications server 11 or the main processing unit 10, and can also be optionally included in the hard disk drives of the remote CPUs. The main processing unit 10 may preferably also have fault tolerant file servers using standard disk drives or redundant arrays of disk drives. The communications server 11 is linked to said main processing units file server by data lines receives and sends data to the remote CPUs 16.

The remote CPU 16 at each location can be dedicated to the present system or can be a multi-task operating system such as those commonly used in office environments. It will be understood by those skilled in the art that the hardware selected, configured and integrated in the present system can vary, as the multiple users of the present system may have different computer systems and known technologies allow for interconnection and communications interchange by and between different hardware systems through common protocols, including but not limited to computer networks interconnected by TCP/IP generally referred to as the Internet.

Data regarding prospective, current and past patients is transmitted to and from the file servers of the main processing unit 10 and the CPU's 16 at each location. As information is obtained from patient prospects and patients, and from the medical practitioner's office, it may be entered into and retrieved from the system through various forms of input/output devices operatively connected to the main processing unit 10 and each of the remote CPUs 16, such as typing on keyboards, speech to text transcription methods, use of digitizers and scanners and other known methods. Information is displayed in various formats and can be viewed on the display devices 12 and 17 or printed using printers 13 and 18.

The system in a preferred embodiment also has tiered secure access. Personnel using the system must clearly demonstrate their identity using a variety of methods depending on the system configuration. Single and multiple passwords, smart card technology, magnetic card or other personal identification technologies can be utilized for this capability. The user's identity establishes the individual "rights" to use various functions. For example, physicians may be the only users given rights to generate prescriptions, nurses could have rights to implement various medical procedures, clerks might need rights to order labs, but records clerks may be limited to changing demographic information. When smart cards are used, the system is available only while a proper, authorized card is inserted. Upon withdrawal, the system completes any processes and reverts to a non responding mode.

The data storage capability of the main processing unit 10 in a preferred embodiment comprises read-only memory connected by data and address bus lines to a random access memory and a system database mass storage device 21. As with other computer systems, the read-only memory provides software instructions to enable the main processing unit 10 to execute necessary software applications programs performing system functions, including, by way of example but not by way of limitation: communications with remote CPUs 16, patient data management, searching and updating; event-driven algorithms through which the system processes requests, actions and instructions to and from medical practitioners, medical facilities, patients, third-party lenders, insurers and others as indicated by user actions ("events") such as pressing keys or clicking a mouse; patient information kit configuration and order fulfillment processing; procedure financing transaction processing; and productivity and sales report generation.

The main processing unit 10 in a preferred embodiment includes proprietary data base structures and information processing algorithms to store and process a comprehensive array of prospective, current and past patient demographics including contact information, biographical information, religion, clinical information, health habits or problems, psychological/psychiatric information, financial and credit information, insurance/employer/other third party payor information, patient attitudes toward medical procedure and other relevant and useful information. With insurance companies and government agencies that are equipped, automatic electronic insurance verification is also possible. The main processing unit 10 also includes a pre-configured and adjustable cycle of actions and communications routines, described further below, to be completed in each patient's case, and generates reminders and prompts to the relevant acting party participating in the system to attend to such actions and tasks.

Patient histories and current conditions are collected by accessing a series of screens providing a comprehensive selection of medical facts on allergies, past medical history, family history, social history and a comprehensive review of systems which can be easily selected to indicate positive responses and, where appropriate, pertinent negative responses.

Integrated patient materials are automatically produced and packaged based on the assessment of the patient's characteristics, medical practitioner recommendations, and the system's guidelines under its proprietary protocols. Materials can be added or deleted from the queue before printing. Materials are gathered and attractively presented in the form of kits 190 which are then sent to the patient on an expedited basis. Materials included in the preferred embodiment of the present system include information and support to patients undergoing medical procedures, including self-care regimes and recommendations, with the goal being to ensure that they have accurate expectations regarding the procedure to be undergone, reducing anxiety and improving confidence, leading to a better outcome, and to also reduce patient hesitancy in deciding to undergo procedures through positive reinforcement and persistent follow-up communications to resolve patient questions. This systematic presentation and delivery of customized information to patients also streamlines the medical practitioner's delivery of elective and/or aesthetic healthcare by performing the beneficial communicative services frequently not delivered by the busy practitioner who often assumes that patients have more knowledge about the procedure undergone than they actually have.

Figure 19:
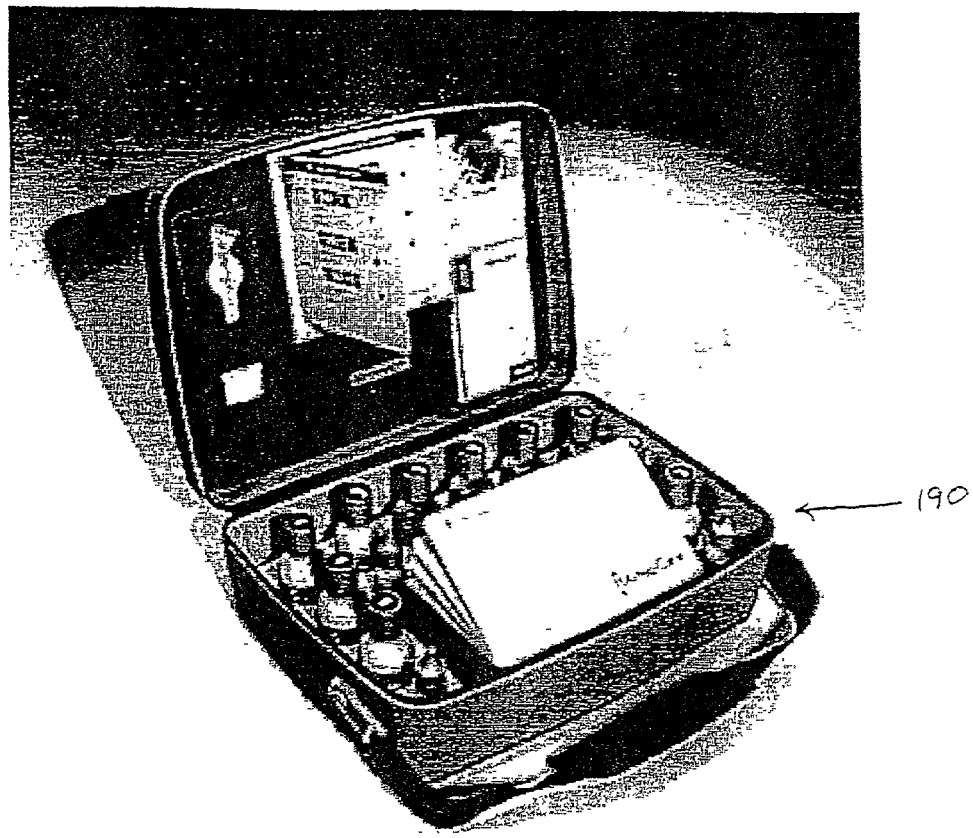
FIG. 19 depicts a sample information and medicament kit produced and used in the present system.
Figure 20:
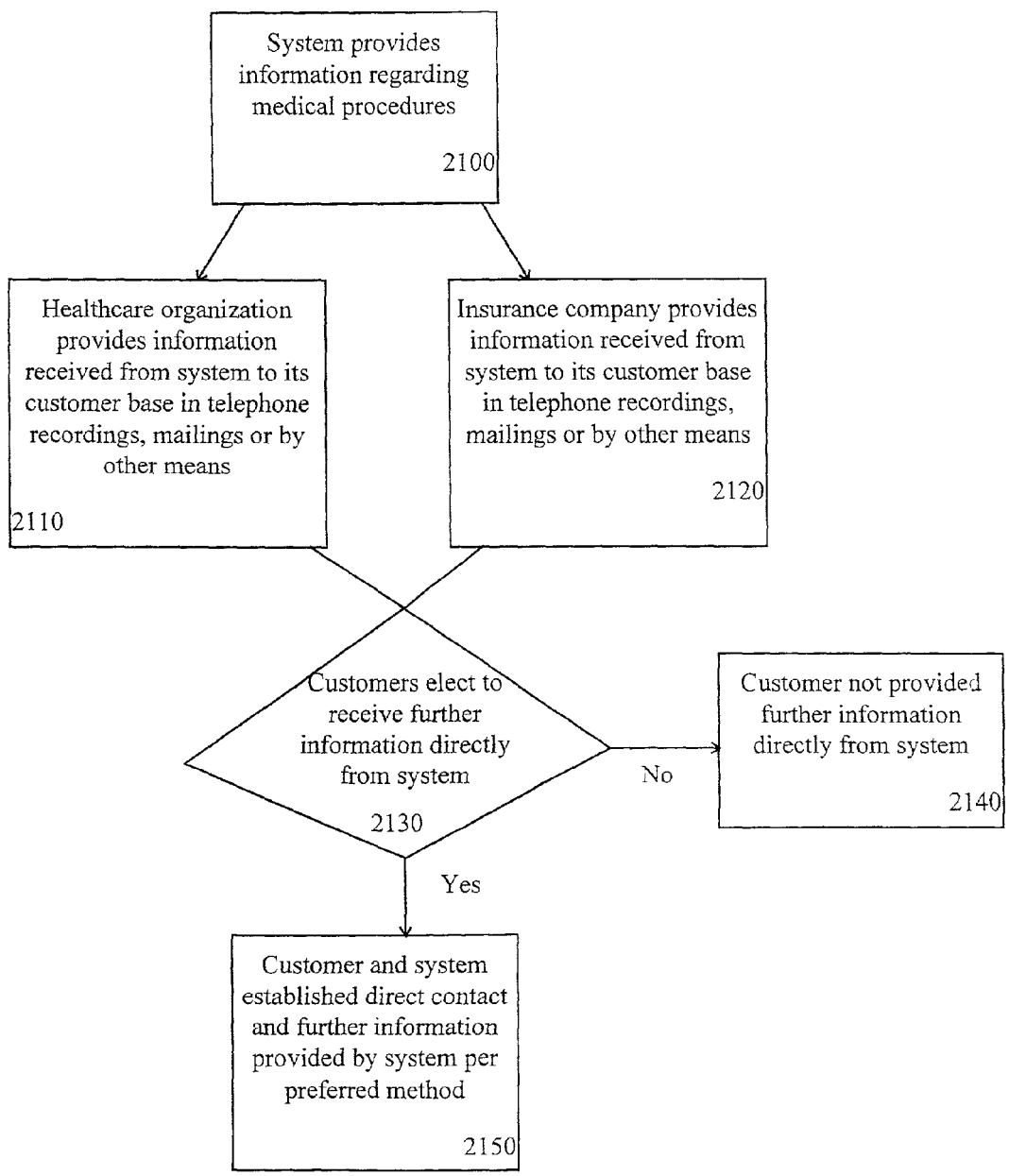
FIG. 20 describes the marketing process flow of the method of the present invention in a preferred embodiment.

The kits 190 assembled through the system provide clear, concise information about the available procedures and options, including frequently asked questions sheets, biographical information about their selected medical practitioner, including curriculum vitae highlights such as years in practice, board certifications, hospital affiliations, a detailed map with directions to the medical practitioner's office, information regarding the selected medical practitioner's appointment times, including the patient's scheduled appointments and a description of what will take place and which staff members will be involved, photos of the medical practitioner and his/her staff members together with introductions of each and a description of their functions, results from lab tests, information concerning special food/diet/medicinal requirements and recommendations, and the price ranges of other procedures. The kits 190 can further include various pre procedure therapeutic medicaments appropriate for the particular procedure. FIG. 19 contains a representative depiction of one embodiment of such kits.

The system provides psychological positive reinforcement to patients at the pre-operative stage by providing a personalized welcome letter from the medical practitioner to the patient, an orientation of the various support and information services made available through the system, patient testimonials, recommendations on planning for the procedure with family, the work place and others, and statistical information on the number of procedures being performed, to give the patient a sense of belonging to a community of individuals committed to looking and feeling their best.

The communications process provides patients with a feeling that they know their medical practitioner and they know about the procedure they are going to undergo, including its costs and what they can expect to happen from start to finish, including pre-procedure preparations and post-procedure recovery. This increased level of information gives the patient greater confidence and reduces anxiety over the procedure. This psychological benefit improves patient satisfaction and improves the overall outcome of the procedure being undergone.

Figure 2:
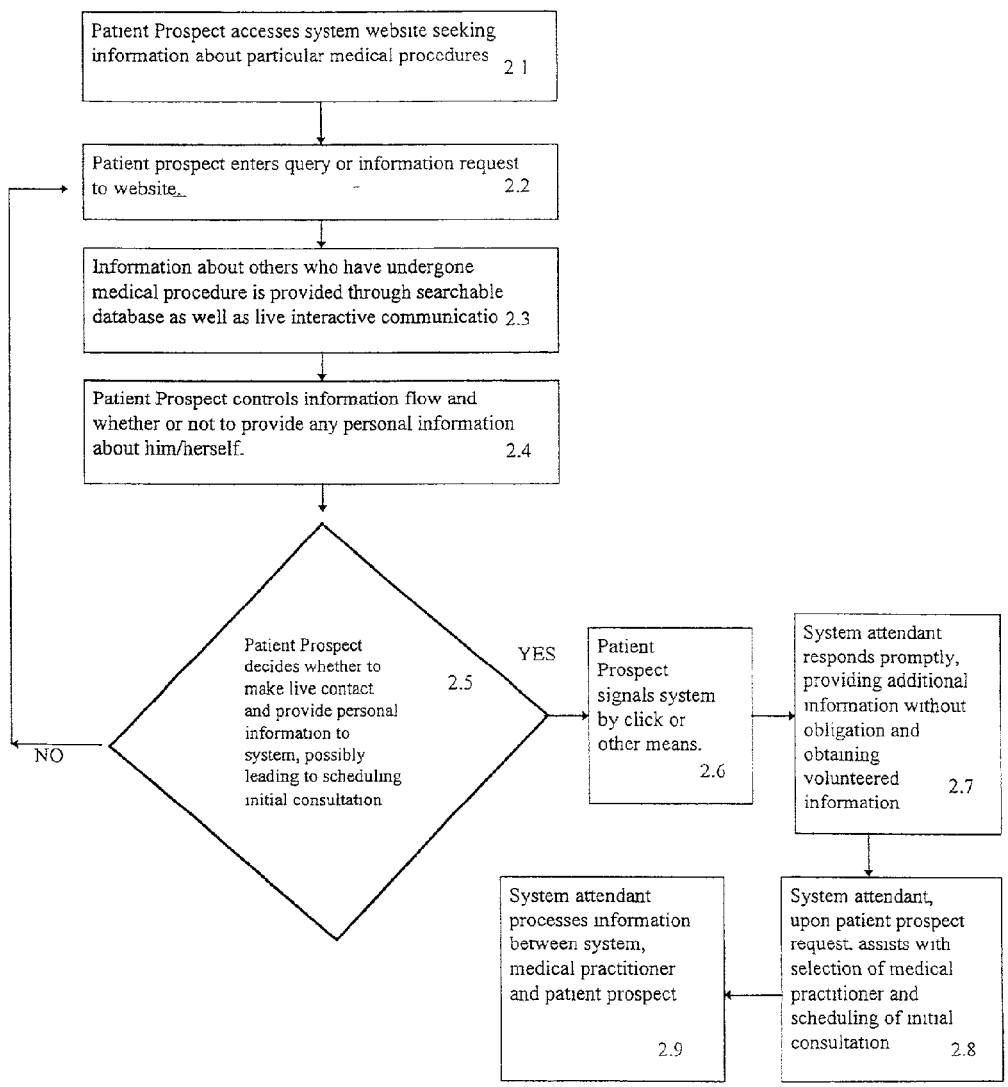
FIG. 2 is a flow chart diagram describing the process flow of the initial information delivery and permission marketing process.

Referring now to FIG. 2, which depicts one embodiment of the present method and system at the stage prior to the initial patient prospect contact stage, in which the patient is seeking information but has not yet decided to go further. Information is made available to patients through an Internet web site, preferably having a searchable database. The website provides information about people who have undergone various elective and/or aesthetic medical procedures. Users of the website do not have to register or otherwise provide personal information in order to use the website. However, the option of obtaining additional information, such as by communicating with a live person and disclosing personal information about themselves to enable them to obtain more tailored information is made available. The decision to take such a step remains with the user of the system at all times, and the user is not pressured. Users access the system website 2.1 through the Internet by entering the system website address using generally known procedures. Users can enter queries to obtain information about other people having similar demographics and have undergone particular medical procedures in particular geographic areas with particular medical practitioners. The information that can be obtained by such queries 2.3 includes anonymous accounts of other people's experiences in having undergone various medical procedures, among various other types and forms of information. By maintaining anonymity, the providers of accounts of their experiences can express their opinions freely without the fear of being identified, which opinions can also include evaluations of medical practitioners.

If a user decides to provide some personal information, such as, for example, geographic location, age, financial status, procedure under consideration, clinical information, contact information, among other types of information, information that is more tailored to the specific circumstances of the user is provided. Any personal information provided by the user is stored for future use in the event the user decides to make contact with a live person.

If a user decides to establish contact with a live person 2.5 to discuss the possibility of undergoing an elective and/or aesthetic medical procedure, the person can indicate this by leaving an email message 2.6, clicking on an icon on their computer screen, or otherwise providing a signal via their computer system. The user is then contacted promptly 2.7 by a live attendant that will have any previously provided identifying information regarding the user. The live attendant provides additional information as requested by the user, again without obligation or pressure. The attendant can be accessed any number of times without charge or obligation to reinforce the feeling in the mind of the user that he or she can trust the system and is not being forced into a procedure he or she does not feel ready for or does not yet want others to know he or she is considering.

The attendant can, when the user requests, assist with the selection 2.7 of a medical practitioner and coordinate scheduling of an initial consultation with the selected medical practitioner, and thereafter transition the patient to a pre and post operative care system and method, one embodiment of which is described below 2.8.

Referring now to FIG. 3, the process flow of steps of the system of the present invention are described from the initial patient prospect contact stage through post-procedure stages. Additional details regarding the steps of the system and method at each of the various stages of the process are described in FIGS. 4–18. Initial patient prospect contacts can be handled by the system of the present invention in various ways and ran occur via in-person communications (patient-prospect walk-ins), via voice telephone or facsimile communications, via computer communications, or other methods. Initial calls by patient prospects can be processed directly to the medical practitioner's office where the practitioner's staff receives and responds to the call, taking preliminary information and advising the caller that a representative from the system representative end of the present system will be contacting the caller within 24 hours.

Alternatively, initial calls can be processed directly to the medical practitioner's office but forwarded from there, either automatically or manually upon identification of the caller as an initial patient prospect caller, to the system where the call is received and responded to by a system representative. The call forwarding means can be telephone call forwarding systems known in the art. Alternatively, initial calls can be diverted automatically by a telecommunications switching/routing device programmed to filter and transfer calls originating from unrecognized telephone numbers to the system. Calls originating from recognized telephone numbers can be routed to the medical practitioner's office to be handled by the medical practitioner's staff as recognized numbers can be identified 28 as calls other than patient prospect initial calls. The system contains hardware and software components to capture 26 and store 30 the caller's telephone number, the name of the record owner of the telephone number from which the call was placed, date and time of call, duration of call, the medical practitioner to whom the call was placed and other pertinent data capable of automatic recording.

For calls switched or transferred to the present system, a system representative assigned and trained to respond to calls placed by patient prospects and patients of the specific medical practitioner will respond and communicate with the patient prospect. The automatically recorded information regarding the call, such as information regarding the medical practitioner to whom the call was placed and the caller's telephone number and identification, will be transmitted 27 with the telephone call through the system to the system representative's CPU 15, so that the call and the call data reach the system representative approximately simultaneously 31, through integration of telephony and computer systems, or other known methods. For calls that are switched or routed to the system, the routing should be transparent to the caller, so that it appears to the caller that he or she is communicating with the medical practitioner's internal staff.

System/patient interaction will be through a single point of contact thereafter, with a system representative and later a nurse assigned to the particular patient to maximize familiarity and service. All subsequent patient prospect/patient calls 29 will be automatically routed to the system and specifically, to the system representative that handled the initial call, by caller identification systems using the information obtained and recorded from the initial call. Subsequent calls will also be handled using appropriate scripted protocols for information delivery and answering of patient/patient prospect questions.

In the initial call, the prospective patient will be queried regarding personal and credit information about him/herself 4.2. In the course of the conversation, the patient is asked whether to schedule an initial consultation. A structured questioning protocol 4.2, discussed further below, is accessed and utilized by the system representative, and responses are inputted and stored. As noted in FIG. 4, when calls are handled by the medical practitioner's internal staff, the medical practitioner's staff then electronically transmits 4.1 the prospective patient's information to the system. Because this information is sensitive, it may be sent in encrypted form. In these situations, the system representative then contacts the prospective patient and thanks the patient for his or her interest and obtains information regarding the patient's medical status, personal and demographic information, psychological/psychiatric informtation and financial/credit information 4.2. A representative questioning protocol for this initial communication is included in Appendix A of this Specification. The protocol is designed to obtain information in a professional and pleasant manner without offending the patient prospect.

Referring to FIG. 3, through this initial questioning protocol, the patient prospect is queried for information that will be used to develop an initial patient profile, to be documented in a patient profile form 101, including a psychological, clinical and financial assessment, as well as a gauge of the patient prospect's attitude toward medical procedure and quality of life issues (such as obesity, or drinking/smoking/drug habits). Patient prospects are categorized based on the assessment as those who are appropriate candidates for the procedure under consideration and those who are not (if not indefinitely, then at least presently) appropriate candidates but who would benefit from information, products and ancillary services. The patient profile is updated throughout the procedure process, and is also used by medical practitioners as a basis for identifying other products and services that the patient may desire or need. Patient profile form 101 summary 102 information can be shared among cooperating practitioners in other specialties that have treated or will treat the same patient for their use in identifying other products and services to market to the patient. The system representative determines whether the prospective patient requires financing and can qualify for financing of the procedure under consideration. The patient is asked whether he or she has any questions or concerns that he or she would like to discuss, and if there are questions or concerns, they are addressed by the system representative. The prospective patient's credit information is electronically transmitted 5.2 to a third party lender, which reviews said information and responds electronically to the system representative with an approval or rejection. The system representative explains to the patient that he/she will be receiving a kit containing a set of personalized pre-procedure information materials and products. The system representative then releases said kit to the patient prospect.

Figure 4:
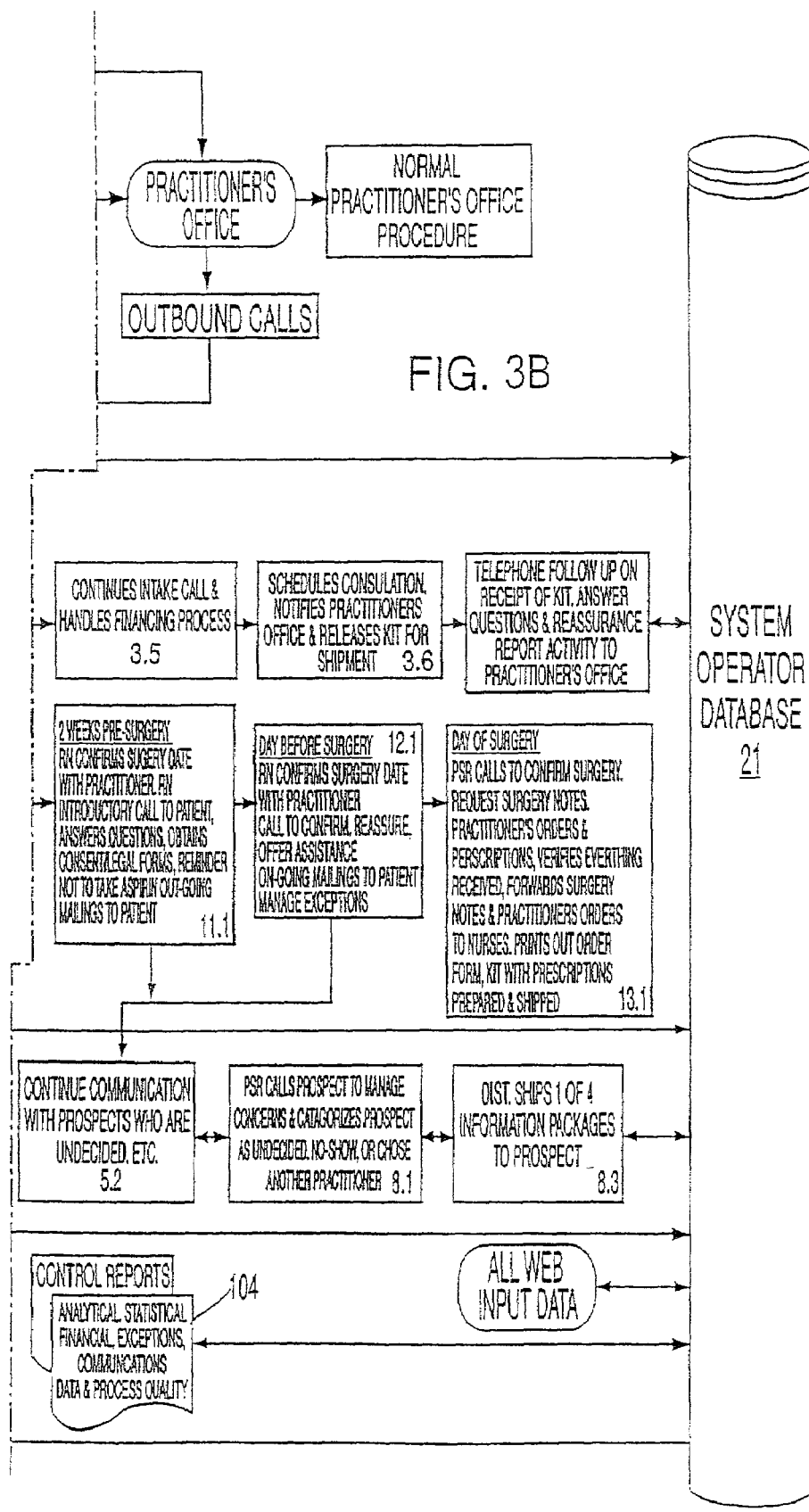
FIG. 4 describes the steps of a preferred embodiment of the present system at the initial patient prospect call to the medical practitioner.

Referring to FIG. 4, the package 4.7 sent to the patient prospect includes an introduction letter from the contacted medical practitioner, including a welcome card, the medical practitioner's biographical summary and photograph. Also included is a map locating the medical practitioner's office, a brochure regarding the pros and cons of undergoing the procedure being considered, a video explaining how the system functions to serve the patient's needs, a summary sheet of the services provided through the system, a consent form to authorize processing of the patient prospect's financing application, and typical pre and post procedure photos for the relevant procedure.

Figure 5:
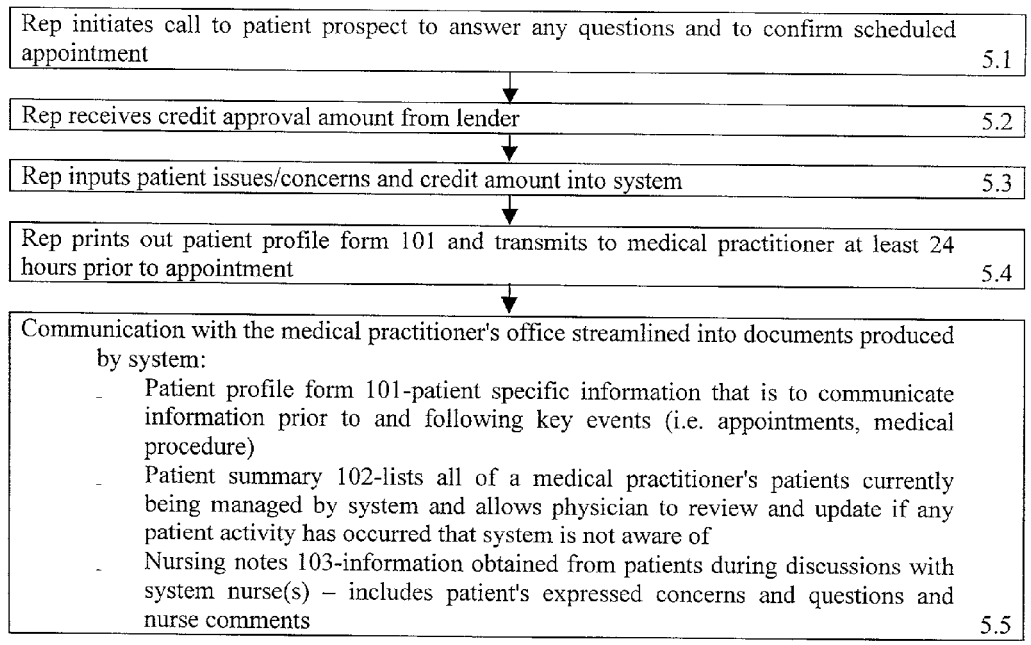
FIG. 5 describes the steps of a preferred embodiment of the present system at the follow up of initial patient/medical practitioner contact in the pre-appointment stage.

Referring now to FIG. 5, if the patient prospect has scheduled an initial appointment with the selected medical practitioner, the system representative contacts 5.1 the patient at least 24 hours prior to the scheduled appointment to confirm the appointment and to answer any questions that the patient may have. The system representative also describes what can be expected to occur at the appointment. By then, the patient prospect's financing application has been processed and the patient prospect's credit approval amount has been transmitted from the third party lender to the system representative. The system representative inputs a record of the patient prospect's concerns and questions 5.3 and the system generates an updated patient profile form 101 indicating the patient's personal, demographic, medical and credit approval information as well as the patient's noted questions and concerns. The patient profile form 101 is then transmitted 5.4 to the medical practitioner at least 24 hours prior to the appointment.

Referring now to FIG. 6, the system transmits a copy of the patient profile form for the patient to the medical practitioner's staff on the day of the scheduled appointment prior to the appointment time. After the patient prospect and the medical practitioner have completed the appointment consultation, the medical practitioner's office transmits to the system a patient summary 102 indicating whether the patient prospect remains undecided, has decided not to undergo the procedure, failed to show up at the medical practitioner's office for the scheduled appointment, or has decided to undergo the procedure and has scheduled a medical procedure date. Should the prospect/patient not want to commit to the procedure during the consultation, the system representative will note the reluctance in the patient summary 103 and patient profile form 101. The system representative will initiate a call to the prospect/patient to access concerns and resolve issues 6.2. The system representative will try to salvage the situation. If the prospect/patient will not go forward, the system representative will categorize the situation as "no show," chosen another medical practitioner, undecided, etc. and release the appropriate information package for shipment by distribution to the prospect/patient 6.5. Follow ups with the prospect/patient will be scheduled in the database and the system will generate reminders to call based on the predefined schedule the system representative entered into the database. A patient summary 102 will be generated and sent to the medical practitioner.

Figure 7:
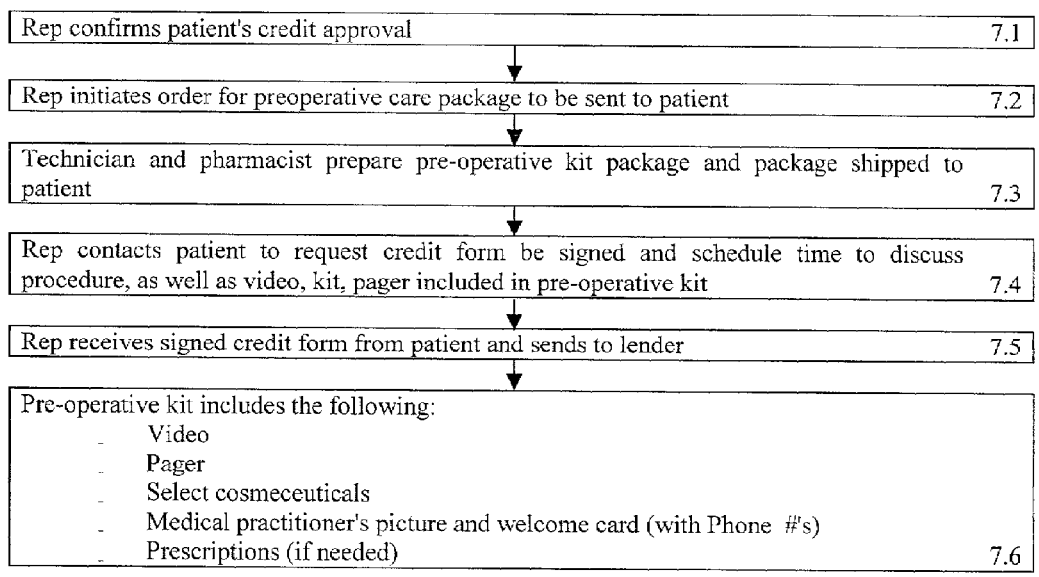
FIG. 7 describes the steps of a preferred embodiment of the present system at the post-first appointment stage for patients who schedule a medical procedure date.

If the patient prospect has scheduled a medical procedure date, the medical practitioner will also transmit the prescribed pre-operative medicament and care regime to the system. The medical procedure date and pre-operative medicament and care regime prescription information is calendared on the system and a pre-operative contact schedule is generated 8.1. As indicated in FIG. 7, the system representative confirms the patient's credit approval 7.1 with the third party lender and generates a stocking list in accordance with the medical practitioner's pre-operative medicament and care prescription for use in assembling a pre-operative medicament and instruction kit. Once assembled, said kit is shipped 39 to the patient.

The pre-operative medicament and instruction kit includes a video explaining the procedure and what to expect from start to finish, a pager which the patient is instructed to carry in order to receive electronic messages from the system, cosmeceuticals, neutraceuticals and other prescriptions in accordance with the medical practitioner's prescription and a contact information card containing the medical practitioner's and the systems telephone numbers.

Referring now to FIG. 8, the system representative verifies 8.1 delivery of the pre-operative kit by contacting the patient and discusses with the patient the outcome of the appointment as well as what to expect through the procedure. The system representative also explains to the patient the contents of the pre-operative kit and how it is used. This repeated follow up provides positive reinforcement to the patient, so that the patient feels well-informed and supported. The system representative also transmits an updated patient profile form 101 and/or patient summary 102 to the medical practitioner including confirmation of delivery of the pre-operative package.

Figure 9:
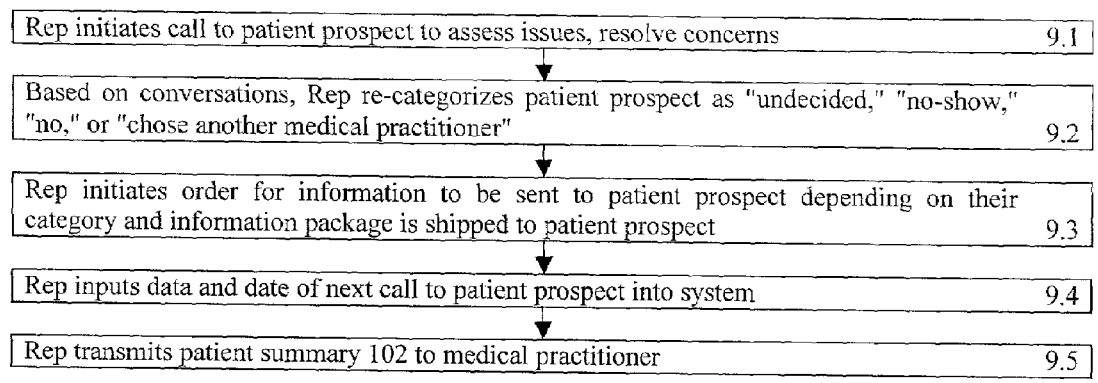
FIG. 9 describes the steps of a preferred embodiment of the present system at the post-first appointment stage for patient prospects that are undecided, fail to show up at the initial appointment, or have chosen another medical practitioner.

Referring now to FIG. 9, the system representative follows up with patient prospects that are undecided or failed to show up at the initial appointment by calling the patient prospect to attempt to assess issues and resolve concerns. Based on the conversations with the patient prospect, the system representative recategorizes the patient prospect as "undecided," "not interested," "chose another medical practitioner" or "interested in rescheduling appointment with medical practitioner." If the patient prospect is interested in rescheduling an appointment with the medical practitioner, the appointment is scheduled with the medical practitioner's office and confirmation sent to both the medical practitioner's office and the patient. The system representative updates the patient profile form 101 and/or patient summary 102 to reflect the rescheduled appointment. The updated patient profile form 101 and patient summary 102 is then transmitted to the medical practitioner. A follow-up call to the patient is also calendared for at least 24 hours prior to the rescheduled appointment. The system representative also produces a patient information package and delivers same to the patient.

Referring now to FIG. 10, when patients cancel scheduled medical procedure, the system representative calls the patient to assess issues and resolve concerns 10.1, and then communicates the patient's concerns to the medical practitioner. Depending on the patient's concerns and the medical practitioner's advice, the system representative produces an appropriate information package and delivers same to the patient 10.3. The system representative then updates the patient profile form 101 and patient summary 102 to reflect the outcome of these discussions with the patient and medical practitioner, calendars a follow-up call 10.4, and transmits the updated patient profile form 101 and patient summary 102 to the medical practitioner.

Referring now to FIG. 11, in the period 10 weeks through 3 weeks prior to the scheduled medical procedure date the system representative calls the patient each week 11.1 to answer any questions and provide positive reinforcement, and inputs patient issues and concerns into the patient profile form 101 and/or patient summary 102. The updated patient profile form 101 and patient summary 102 is transmitted on an as needed basis to the medical practitioner, and comments from the medical practitioner are noted thereon. During this period, the system generates and delivers to the patient informational mailings relevant to the patient and the procedure to be undergone 11.5.

Figure 12:
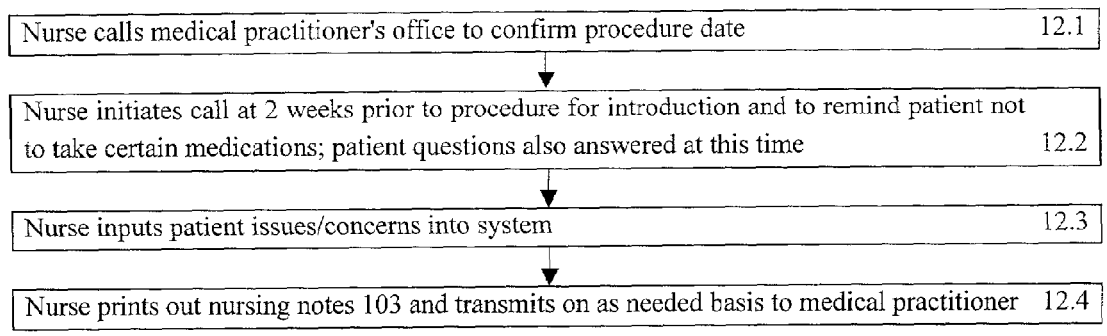
FIG. 12 describes the steps of a preferred embodiment of the present system during the period 2 weeks through the day prior to the scheduled medical procedure date.

Referring now to FIG. 12, in the 2 weeks prior to the scheduled medical procedure date a nurse on the system staff calls the medical practitioner's office as well as the patient to confirm the medical procedure date 12.1 and also introduces herself to the patient and reminds the patient about specific pre-operative tasks to be completed and regimens to be followed during this period 12.2. The nurse also addresses patient issues and concerns and documents same in a nursing notes 103 form that is then transmitted to the medical practitioner's office on an as needed basis 12.4.

Figure 13:
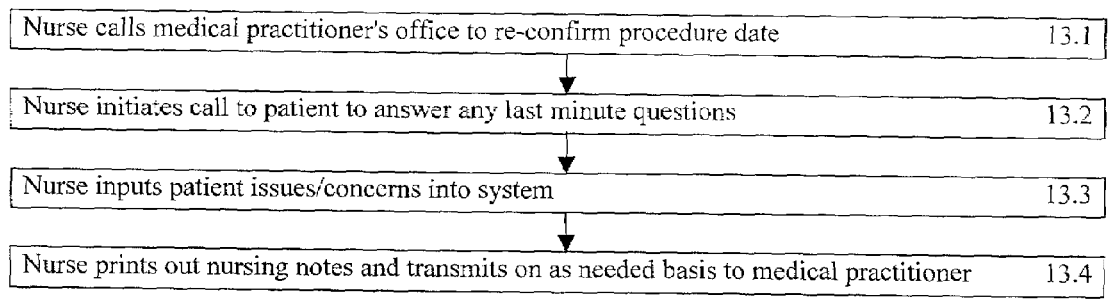
FIG. 13 describes the steps of a preferred embodiment of the present system on the day prior to the scheduled medical procedure date.

Referring now to FIG. 13, on the day before medical procedure, the nurse confirms 13.1 the medical procedure date with the medical practitioner and also contacts the patient to confirm, reassure, offer assistance and discuss informational mailings and concerns.

Figure 14:
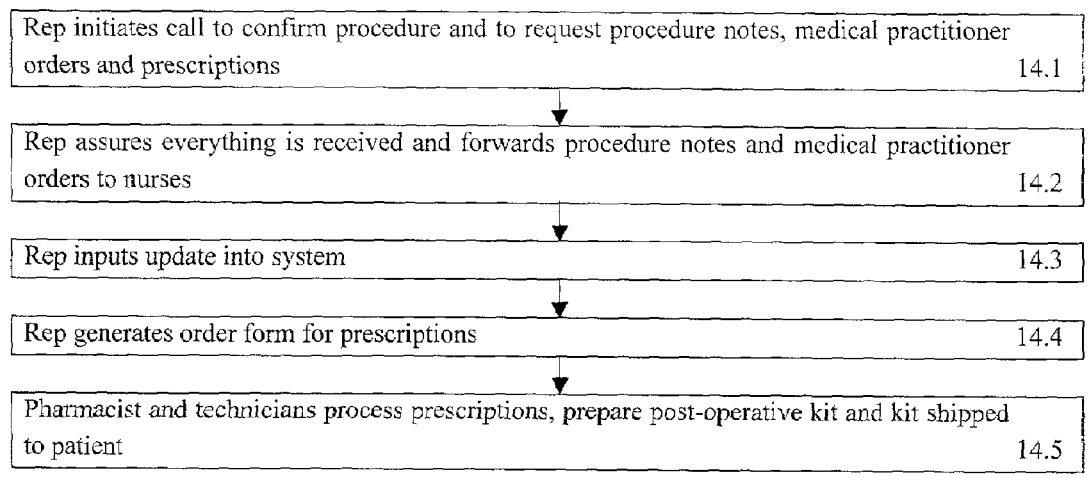
FIG. 14 describes the steps of a preferred embodiment of the present system on the day of medical procedure.

Referring now to FIG. 14, on the scheduled medical procedure date, the system representative contacts the patient, the medical practitioner's office and the offsite facility where the procedure will be performed if the procedure is to be performed in a facility outside the medical practitioner's office to confirm the scheduled medical procedure 14.1. The system representative receives and transmits medical procedure notes, medical practitioner orders and prescriptions to appropriate recipients, confirming receipt of same. The patient summary 102 is updated to reflect this information. The system representative then produces a post-operative treatment kit and delivers same to patient 14.5.

Figure 15:
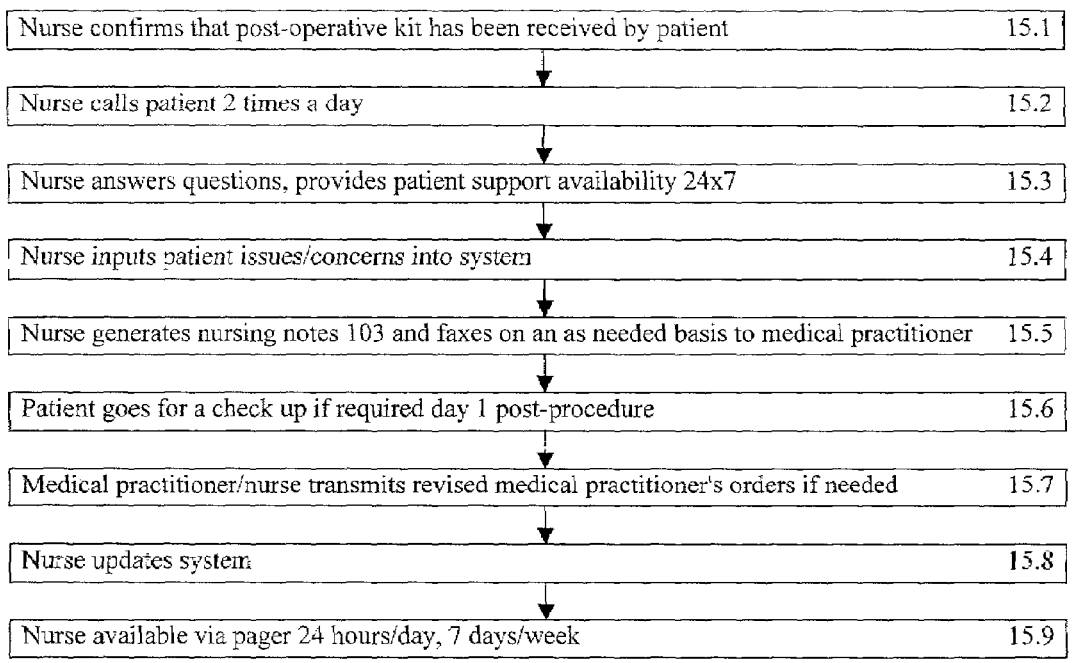
FIG. 15 describes the steps of a preferred embodiment of the present system on the first day post-medical procedure.

Referring now to FIG. 15, on the first day post-medical procedure, the nurse confirms receipt of the post-operative treatment kit by the patient 15.1 and explains its contents and use. The nurse calls the patient twice that day to check the patient's status, remind the patient of what to expect in the post-operative phase, and address any patient questions or concerns. The patient is advised that system support is available 24 hours a day, 7 days a week 15.3. The nurse generates nursing notes 103 and transmits them to the medical practitioner on an as needed basis 15.5. The medical practitioner transmits updated orders if needed to the system 15.7, which then processes them and delivers them to the patient. The first post-medical procedure appointment between the patient and the medical practitioner is scheduled.

Figure 16:
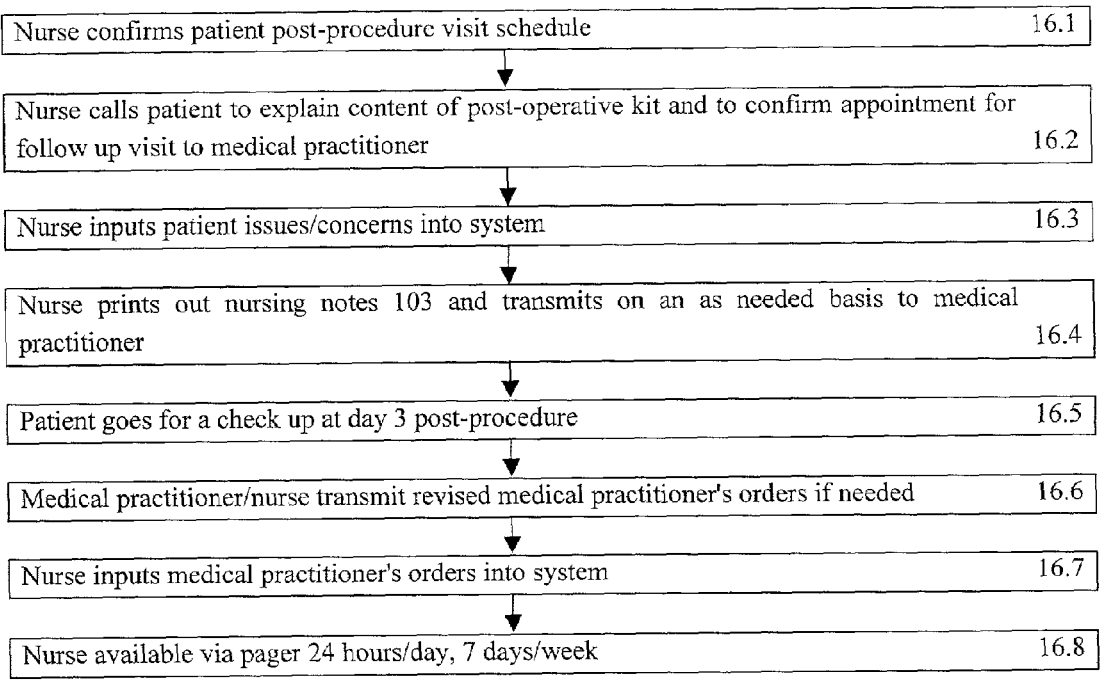
FIG. 16 describes the steps of a preferred embodiment of the present system prior to and on the day of the first post-medical procedure appointment.

Referring now to FIG. 16, prior to and on the day of the first post medical procedure appointment between the patient and the medical practitioner, the nurse confirms the scheduled appointment 16.1 with the patient and the medical practitioner's office and explains to the patient what will occur during the appointment. The nurse addresses any patient questions or concerns and generates nursing notes 103 reflecting the communications with the patient and then transmits same to the medical practitioner on an as needed basis. The medical practitioner transmits any revised orders to the system, which then processes them and delivers them to the patient. The patient summary 102 is updated to reflect all new information.

Referring now to FIG. 17, during the period from day 4 to day 7 post medical procedure, the nurse calls the patient twice a day to answer questions and concerns 17.1. Any patient questions or concerns are inputted into the system and nursing notes 103 are generated and transmitted to the medical practitioner on an as needed basis. The medical practitioner transmits to the system any revised medical practitioner's orders, which are then processed by the system and delivered to the patient 17.5. The patient summary is updated to reflect new information and the nurse or system representative orders and causes to be delivered a token of appreciation and support such as flowers, candy or a hair or makeover appointment 17.6. This is intended to strengthen the patient's positive self-image and positive perception of the overall experience.

Figure 18:
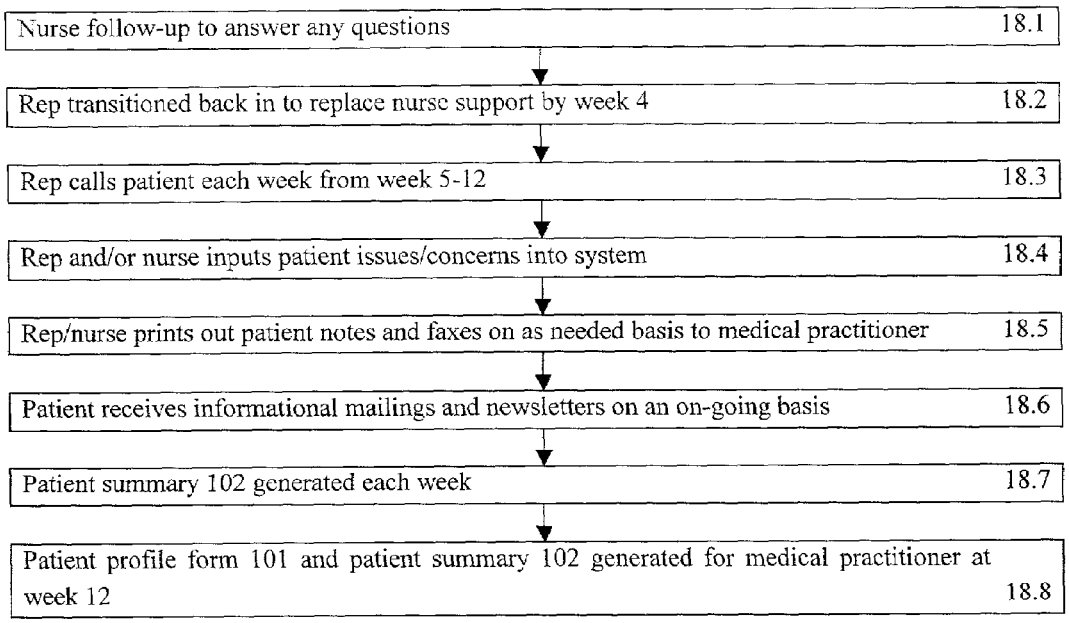
FIG. 18 describes the steps of a preferred embodiment of the present system during the period from week 1 through week 12 post medical procedure.

Referring now to FIG. 18, during the period 1 week to 12 weeks post medical procedure, the nurse calls the patient periodically to follow up and answer any questions 18.1, and after week 4 the system representative rather than the nurse 18.2 the patient on a weekly basis to provide positive reinforcement and answer any questions or concerns. The system generates and delivers informational mailings and newsletters to the patient on an on-going basis. An updated patient summary 102 is generated each week, and a patient profile 101 and patient summary 102 is generated at week 12 18.8. In the interim and on an as needed basis, the system representative transmits updated patient summaries to the medical practitioner.

The present system generates various control reports 104 providing the practitioner with the number of newly registered patients, the number of prospective patients committed to medical procedure, the number of cancelled surgeries and the reasons for cancellations, patient credit-line revenues, product sales and payments, patient trend data such as the number of patients who schedule multiple procedures, patient referral activity, and percentage of increased closure rates. The present system also serves medical practitioners by compiling and providing comprehensive patient histories prior to initial consultation, with additional detailed information pertaining to the patient's expectations and relevant past experiences, incorporating ongoing patient status monitoring reports and patient feedback reports designed to provide meaningful data to help the practitioner refine his/her practice and achieve an improved level of care provision to future patients 105.

The system of the present invention communicates with the patient and the medical practitioner and his/her practice, with labs and ancillary service providers, pharmacies, hospitals, lenders and insurers, and other participants in the healthcare delivery process, and the system representative coordinates all of these communications. Such communications are carried out, or with the other aspects of the present system, by known means including but not limited to electronic computer messaging (e-mail), via facsimile, via the Internet through websites or via voice telephony. The present system's reports also provide means for medical practitioners to review their efficiency and prospect closure rates, and increases of revenues for medical practitioners through the facilitation of procedure financing through third party lenders and through sales of pre-operative and post-operative products and services.

While the present invention has been shown and described herein in what are considered to be the preferred embodiments thereof, illustrating the results and advantages over the prior art obtained through the present invention, the invention is not limited to those specific embodiments. Thus, the forms of the invention shown and described herein are to be taken as illustrative and other embodiments may be selected without departing from the spirit and scope of the present invention.

APPENDIX A

INITIAL SAMPLE INTERVIEW SEQUENCE 32.1 Segment # 1 (Why Advicare and Confidentiality Issues)

32.1.1 Introduction Module to System Representative ("PSR")

32.1.1.1 Hi, My name is _____, I am your PSR, and I am the designated agent for Medical practitioner _____'s office.

32.1.1.2 Medical practitioner _____ has asked that I call you. He/ She feels so strongly about patient relationships that he/she is involved the Advicare Service program. I will be the central point of contact should you wish to move forward in having Dr. _____ evaluate you and possibly be seen for treatment. Our company provides all aspects of education, coordination and administrative services relating to your potential consultation and follow-up appointments with Dr. _____. There is no cost to you, all costs are borne by the medical practitioner and all information will only be shared between you and the medical practitioner in written form and will be available for you to pick up at the office.

32.1.1.3 Patient Service Representative's introduction (PSR)

32.1.1.3.1 (PSR) Name 32.1.1.3.2 How would like me to refer to you (first or last name)

32.1.1.3.3 I am responsible for _____

32.1.1.3.4 I would like to explain the relationship between Advicare, you the Patient, and Medical practitioner _____

32.1.1.4 Overview of telephone time for this educational program 32.1.2 Confidentiality Issues Module 32.1.2.1 Why we ask these questions 32.1.2.2 How it will help the process 32.1.2.2.1 Optimize your visit 32.1.2.2.2 Medical practitioner needs to know about your specific concerns in advance so the medical practitioner can better prepare for your consultation 32.1.2.2.3 Reduce anxiety 32.1.2.2.4 Questions that you would like to ask will be detailed now when you are calmer rather than at the Medical practitioner's office where you may forget certain questions.

32.1.2.3 We will purge the clinical data from our system after 30 days and how by law we can not or will not share any information with anyone else.

32.1.2.4 We will forward a complete report to you by mail or you can pick it up at the medical practitioner's office upon your visit.

32.1.2.5 If there is other data that you wish to have us know or change before your visit, please fell free to call us.

32.1.2.6 Our phones are open to you 24 hours a day; there is no cost to you, this service is made available to you through Dr. _____ office 32.1.3 Introduction to Medical practitioner/ Advicare Partnership Module 32.1.3.1 Getting In to See Your Medical practitioner Now 32.1.3.1.1 Special Slots Times for Advicare's Patients 32.1.3.2 How the Patient Satisfaction Guarantee Program operates 32.1.3.2.1 Time 32.1.3.2.2 Cost 32.1.3.2.3 Products & Usage 32.1.3.2.4 Compliance 32.1.3.2.5 Yearly Visits 32.1.3.2.5.1 (Free of Charge)

32.1.3.3 We are a single point of distribution 32.1.3.4 We are not your medical solution, merely a conduit of information from the many people at Dr. _____'s Office ___ would be providing services, care and information to you.

32.1.3.5 We are staffed with nurses, PSR, pharmacists and other allied health care professionals; we will be your advocates in the process. We will provide solutions to you in advance of your request and will always be available to assist you insuring your procedure goes as smoothly as possible.

32.1.3.6 We will inform the medical practitioner as requested about the status of your pre and post operative care. We will interface will all the professionals at their offices to insure you receive information and care as quickly as possible.

32.1.3.7 Our Phone Numbers 32.1.3.8 Our Website 32.2 Segment # 2 (Patient Prospect Education Process)

32.2.1 Basic Patient Prospect Information Module 32.2.1.1 Acquisition of Name, Address, Phone Number Information 32.2.1.2 Soft Sales Efforts 32.2.2 Background On Medical practitioners Module 32.2.2.1 CV highlights 32.2.2.2 Years in Practice 32.2.2.3 Number of total Procedures Performed 32.2.2.4 Number of Particular Procedure Performed 32.2.2.5 Board Certification in which Specialty 32.2.2.6 Staff, Names and Function 32.2.2.7 Trained where with hospital affiliations at _____

32.2.2.8 Patient Testimonials about Medical practitioner 32.2.2.9 Medical practitioner's Age 32.2.3 Education Module 32.2.3.1 Education on Various Procedures 32.2.3.1.1 The following procedures would be available to you 32.2.3.1.2 Procedure A, B, etc.

32.2.3.1.2.1    Of course after your visit with the medical practitioners the Dr. _____ will make the final decision 32.2.3.1.3    Education on Requested Procedure 32.2.3.1.4    Price Range 32.2.3.1.5    Recuperation time 32.2.3.1.6    Preparation time 32.3    <u>Segment #3 (Interest in Other Procedures)</u>

32.3.1   Do you wear eyeglasses?

32.3.2   Do you exercise regularly, do you want more information?

32.3.3   Do you eat properly, do you want more information?

32.3.4   Are you interested in any other procedures?

32.4    <u>Segment # 4 (Patient Advocacy Position)</u>

32.4.1   Advicare Services Module 32.4.1.1    24 X 7 Support Availability 32.4.1.2    AdvoKits 32.4.1.3    Tapes, Video, Audio 32.4.1.4    RN's Backgrounds 32.4.1.5    Pharmacist's Backgrounds 32.4.1.6    AdvoNet review 32.4.1.7    AdvoCard review 32.5    <u>Segment # 5 (Patient Prospect Interview)</u>

32.5.1   Financing Module 32.5.1.1    Hard Sales Efforts 32.5.1.2    Referral 32.5.1.3    Warm Transfer 32.5.2 Medical Profile Module 32.5.2.1 Medical History sub-module 32.5.2.1.1 Family medical history 32.5.2.1.2 Allergies to medication 32.5.2.1.3 Have you had any experience with medical procedure in the past?

32.5.2.1.4 Prior hospitalizations 32.5.2.1.5 Any difficulty with healing 32.5.2.1.6 Any tendency to scar abnormality (keloid)

32.5.2.1.7 How would you rate your healing capability 1-10 10 being the fastest.

32.5.2.1.8 Diabetes 32.5.2.1.9 Hypertension 32.5.2.1.10 Review of Body Systems, Please answer "Yes" or "No," should any significant concerns appear your the medical practitioner will discuss them with you. (Q/A on Status of Each)

32.5.2.1.10.1 Cardiac (circulatory)

32.5.2.1.10.2 Pulmonary 32.5.2.1.10.3 Renal 32.5.2.1.10.4 Urologic 32.5.2.1.10.5 Gastrointestinal 32.5.2.1.10.6 Infection Disease / Immunodeficiency 32.5.2.1.10.7 Endocrine 32.5.2.1.10.8 Neurologic 32.5.2.1.10.9 Autoimmune Disease 32.5.2.1.10.10 Special Senses

|  |  | 32.5.2.1.10.10.1 | Hearing |
|---|---|---|---|
|  |  | 32.5.2.1.10.10.2 | Eyes |
|  |  | 32.5.2.1.10.10.3 | Taste |

32.5.2.1.10.11    Psychiatric 32.5.2.1.11    Psychological expectation's sub-module 32.5.2.1.11.1    Why do you wish to undergo this procedure?

32.6   <u>Segment #5 (Questions & Answers from Patient Prospect)</u>

32.6.1    Are there other family members that might have questions for us to answer? If so, please feel free to have them contact me.

32.6.2  Appointment Module 32.6.2.1    Confirmation of Existing Appointment with Advicare Medical practitioner 32.6.2.2    Generate new appointment for Advicare's Medical practitioners Office 32.7   <u>Segment #7 (Appointment Module)</u> -- Schedule appointment for patient prospect at Medical practitioner's office -- confirm 32.8   <u>Segment #8 (Fulfillment Module)</u>

32.8.1  Mailing/Fulfillment Overview 32.8.1.1    Best time to call prospect 32.8.1.2    Demographic Information 32.8.1.3    Other Numbers 32.8.1.4    Fax Numbers 32.8.1.5    E-mail 32.8.1.6    Location to send mail/package 32.8.1.7    Our hours of operation 32.8.2 Mailing Sub Module 32.8.2.1 Personalized letter of Welcome 32.8.2.2 Testimony on Advicare 32.8.2.3 Map to medical practitioner's office 32.8.2.4 Appointment time 32.8.2.5 Who they will see, staff persons and names 32.8.2.6 AdvoCard Application for signature 32.8.2.7 Marketing on why to use Advicare's Program 32.9 Segment #9 (Closing Module)

32.9.1 Insure patient prospects understand that there is no cost to the prospect, all cost are borne by the medical practitioner and all information will only be shared between the prospect and the medical practitioner in written form.

32.9.2 Inform they will receive a letter from us on the appointment date and a map along with other information.

32.9.3 Indicate that we will contact them to insure that they have received the package we have shipped.

32.9.4 Indicate that we will call them 24 hours in advance of appointment.

32.9.5 Call us with any questions any time, before you arrive at the medical practitioner or after you return.

32.9.6 By the way, you will love Dr. \_\_\_\_\_; he/she was a great choice on your part.

32.9.7 Thank them for their time.

Having thus described the invention, what is claimed is:

1. A system for providing support and care to persons considering or undergoing a medical procedure, comprising:

means for a third party provider to receive, process, and provide information between at least one person and at least one medical practitioner;

means for the third party provider to pre-qualify financing for at least one medical procedure under consideration by said person by said third party provider using said information;

means for financing said medical procedure by said third party provider;

means for paying a portion of a fee charged by said medical practitioner for said medical procedure to said third party provider in exchange for said third party provider bringing together said person and said medical provider for said medical procedure which is financed by said third party provider;

means for said third party provider to provide information and positive reinforcement to said persons regarding said medical procedure being considered or undergone, means for said third party provider to schedule and coordinate medical consultations and said medical procedure between said person and said medical practitioners; and means for said third party provider to receive, process, and deliver care orders and medicaments from said medical practitioners to said persons.

2. The system of claim 1, further comprising means for said third party provider to monitor said persons'adherence to said medical practitioner's care orders, medical consultation and medical procedure schedules and medicament prescriptions.

3. The system of claim 1, further comprising:

means for said third party provider to schedule said medical procedure between said person and medical practitioner; and means for said third party provider to receive, process, and deliver care orders and medicaments from said medical practitioner to said person.

4. The system of claim 1, further comprising means for said third party provider to request and obtain said persons'insurer or other third party payor authorization for payment of said medical consultations and procedures.

5. The system of claim 1, further comprising means for processing data regarding sales of medicaments and completion of financing transactions for said medical procedure by said medical practitioner and processing of payments due to said medical practitioner based on said sales of medicaments and financed procedures.

6. The system of claim 1, wherein said means for said third party provider to receive, process, and provide information regarding said person further comprises a network of computer systems.

7. The system of claim 1, wherein said means for said third party provider to receive, process, and provide information regarding said person further comprises a voice telephony system permitting communication between said medical practitioner and said patient.

8. The system of claim 1, wherein said means for said third party provider to receive, process, and provide information regarding said person further comprises a facsimile communications system permitting communication between said medical practitioner and said patient.

9. The system of claim 1, wherein said means for said third party provider to receive, process, and provide information regarding said person to and from said person and said medical practitioner further comprises a structured query protocol designed to allow said medical practitioner to assess said person's physical and psychological/psychiatric characteristics in order to identify said person's needs for medical care.

10. The system of claim 1, wherein said means for said third party provider to receive, process, and provide information regarding said person to and from said person and said medical practitioner further comprises a structured query protocol designed to allow said medical practitioner to assess said person's physical and psychological/psychiatric characteristics in order to identify said person's needs for information regarding said medical procedure.

11. The system of claim 1, wherein said means for said third party provider to receive, process, and provide information regarding said person to and from said person and said medical practitioner further comprises a structured query protocol designed to allow said medical practitioner to assess said person's physical and psychological/psychiatric characteristics in order to identify said person's needs for positive reinforcement.

12. The system of claim 1, wherein said means for said third party provider to provide information and positive reinforcement to said person regarding said medical procedure being considered or undergone comprises a website accessible via a network of computer systems connected by common protocols, said website having a searchable database containing information regarding said medical procedure being considered, and wherein information is provided without obligation or requiring person using the system to disclose their identites or other personal information, thereby fostering a sense of comfort and trust in the person considering undergoing said medical procedure.

13. The system of claim 12, wherein said information provided through said website comprises a written narrative of personal experiences of other persons who have undergone the medical procedure under consideration.

14. The system of claim 12, further comprising means for accessing a live attendant that can provide additional information, assist with selection of a medical practitioner and coordinate scheduling of an initial consultation with the medical practitioner which has been selected based upon a request by said person using the system.

15. The system of claim 1, wherein said means for said third party provider to provide information and positive reinforcement to said person regarding said medical procedure being considered or undergone further comprises kits assembled and delivered to said person containing said information.

16. The system of claim 15, wherein said kits include information regarding said medical practitioner who will perform said medical procedure.

17. The system of claim 15, wherein said kits include information regarding self-care measures for said person to undertake.

18. The system of claim 15, wherein said kits include medicaments to be used by said person.

19. A system for a third party provider to provide pre and post procedure support and care to persons considering or undergoing medical procedures, comprising:

a system representative terminal for said third party provider to receive, process, and provide information between at least one person and at least one medical practitioner, the system representative terminal having a central processing unit and a system representative modem, a main processing unit communicating with said central processing unit of said system representative terminal, a communications server interconnected to said main processing unit, a communications server modem interconnected to said communications server, a medical practitioner terminal for said medical practitioner to receive, process, and provide information regarding said person to and from said third party provider, the medical practitioner terminal having a central processing unit, and a medical practitioner terminal modem interconnected to said medical practitioner terminal's central processing unit and communicating with said system representative modem interconnected to said system representative terminal's central processing unit to allow for information transfer between said medical practitioner terminal and said system representative terminal, at least a first information processing algorithm, operable on the main processing unit for a third party lender to pre-qualify financing for at least one medical procedure under consideration by said person, at least a second information processing algorithm, operable on the main processing unit for financing by said third party lender said medical procedure, at least a third information processing algorithm, operable on the main processing unit for paying a portion of a fee charged by said medical practitioner for said medical procedure to said third party provider in exchange for said third party provider bringing together said person and said medical provider for said medical procedure which is financed by said third party lender.

20. The system of claim 19, further comprising
a display device interconnected to said central processing unit of said system representative terminal,
a printer interconnected to said central processing unit of said system representative terminal,
a display device interconnected to said central processing unit of said medical practitioner terminal and
a printer interconnected to said central processing unit of said medical practitioner terminal.

21. The system of claim 19, further comprising a web server interconnected to said communications server to provide for communications between said system representative terminal, said medical practitioner terminal and said person through an Internet connection.

22. The system of claim 19, further comprising one or more third party payor terminals, each having a central processing unit with a modem interconnected thereto to provide for communications between said system representative terminal, said medical practitioner terminal and said third party payor terminals.

23. A method executing on a web server for a third party provider to provide pre and post procedure support and care to persons considering or undergoing medical procedures, the method for said third party provider comprising the steps:

receiving, processing and providing information between at least one person and at least one medical practitioner, pre-qualifying, by a third party provider, financing for at least one medical procedure under consideration by at least one medical procedure for said person, financing said medical procedure by said third party provider, paying a portion of a fee charged by said medical practitioner for said medical procedure to said third party provider in exchange for said third party provider bringing together said person and said medical provider for said medical procedure which is financed by said third party provider, storing the received, processed and provided information regarding said person in a database maintained on a system representative terminal, providing information and positive reinforcement to said person regarding the procedure being considered or undergone, scheduling and coordinating medical appointments and procedures between said person and said medical practitioner, receiving, processing and delivering care orders and medicaments from said medical practitioner to said person, and monitoring said person's adherence to medical practitioner's care orders, appointment and procedure schedules and medicament prescriptions.

24. The method of claim 23, wherein said step of providing information and positive reinforcement to said person regarding the procedure being considered or undergone comprises providing information via a searchable database accessible through an Internet website without obligation or requiring said person to disclose their identities or other personal information, thereby fostering a sense of comfort and trust in said person.

25. The method of claim 23, wherein said step of providing information and positive reinforcement to said person regarding the procedure being considered or undergone further comprises providing a written narrative-of personal experiences of other persons who have undergone the medical procedure under consideration.

26. The method of claim 23 wherein said step of providing information and positive reinforcement to said persons regarding the procedure being considered or undergone further comprises providing access to a live attendant that can provide additional information, assist with selection of a medical practitioner and coordinate scheduling of an initial consultation with the medical practitioner which has been selected based upon a request by said person.

27. The method of claim 23, wherein said step of providing information and positive reinforcement to said persons regarding the procedure being considered or undergone further comprises providing pre procedure and post procedure information and medicament kits assembled based on one or more particular needs and characteristics of said person.

28. A method executing on a web server for a third party provider to deliver pre and post procedure support and care to patients undergoing medical procedures, the method of the third party provider comprising the steps of:

obtaining patient medical, demographic, psychological and financial/credit information prior to a patient undergoing at least one medical procedure, storing patient medical, demographic, psychological and financial/credit information in a database maintained on a system representative terminal, assessing said information to determine patient needs for information, support and financing for said medical procedure, providing information regarding the procedure to be undergone, providing pre and post medical procedure medicaments and self-care orders, providing positive reinforcement to said patient regarding said medical procedure, and coordinating scheduling of medical consultations and said medical procedure between medical practitioners and said patient, pre-qualifying, by a third party lender, financing for at least one medical procedure under consideration by at least one medical procedure for said person, financing said medical procedure by said third party lender, and paying a portion of a fee charged by said medical practitioner for said medical procedure to said third party provider in exchange for said third party provider bringing together said person and said medical provider for said medical procedure which is financed by said third party lender.

29. The method of claim 28 further comprising the steps of obtaining patient financial information prior to the patient's undergoing said medical procedure and assessing said information to determine patient needs for financing for said medical procedure.

30. A system for improving medical procedure outcomes, comprising:

means for a third party provider to receive, process and deliver care orders and medicament prescriptions from medical practitioners to patients, means for said third party provider to receive, process and deliver medical status information from patients to medical practitioners, means for pre-qualifying, by a third party lender, financing said medical procedure under consideration by said person by said third party lender using said information, means for financing said medical procedure by said third party lender, means for paying a portion of a fee charged by said medical practitioner for said medical procedure to said third party provider in exchange for said third party provider bringing together said person and said medical provider for said medical procedure which is financed by said third party lender, and means for said third party provider to schedule and coordinate post-operative medical appointments between patients and medical practitioners and monitoring patient adherence to medical practitioners' care orders and medicament prescriptions.

31. A system for delivering pre and post operative support and care to patients and processing and managing information regarding patients and sales of products and services made to patients, comprising:

means for a third party provider to receive and process personal, medical and financial/credit data pertaining to said patient, means for the third party provider to electronically transmit said patient's personal and medical data to and from medical practitioners, means for electronically transmitting said patient financial/credit data to a third party lender for pre-qualifying medical procedure financing application processing under consideration by said patient, means for financing said medical procedure by said third party lender, means for paying a portion of a fee charged by said medical practitioner for said medical procedure to said third party provider in exchange for said third party provider bringing together said person and said medical provider for said medical procedure which is financed by said third party lender, means for the third party provider to schedule and coordinate medical consultation appointments and medical procedures between said patients and said medical practitioners, and for coordinating said medical practitioners' receipt of payment for said medical consultations and medical procedures through said third party lender upon patient credit and financing approval, means for the third party provider to receive, process, and deliver pre and post medical procedure patient prescriptions for medicaments, procedure information and patient care orders from said medical practitioners to said patients, and means for said third party provider to process data regarding sales of medicaments and completion of medical procedure financing transactions attributable to each said medical practitioner, and calculation of payments due to each said medical practitioner based on said sales and financings.

32. The method of claim 23, wherein said step of providing information and positive reinforcement to said persons further comprises providing means for delivery of information about said medical procedures to customer bases of healthcare organizations and healthcare insurance companies and providing means for said customer bases to request additional information.

* * * * *